US00RE39616E

(19) United States
(12) Reissued Patent
Chorev et al.

(10) Patent Number: US RE39,616 E
(45) Date of Reissued Patent: May 8, 2007

(54) AMINOINDAN DERIVATIVES

(75) Inventors: Michael Chorev, Jerusalem (IL); Tamar Goren, Rehovot (IL); Yacov Herzig, Ra'ananna (IL); Jeffrey Sterling, Jerusalem (IL); Marta Weinstock-Rosin, Jerusalem (IL); Moussa B. H. Youdim, Haifa (IL)

(73) Assignees: Teva Pharmaceutical Industries, Ltd., Petach-Tikva (IL); Yissum Research Development Company of the Hebrew University of Jerusalem, Jerusalem (IL); Technion Research and Development Foundation, Ltd., Haifa (IL)

(21) Appl. No.: 11/091,008

(22) Filed: Mar. 25, 2005

Related U.S. Patent Documents

Reissue of:
(64) Patent No.: 6,538,025
Issued: Mar. 25, 2003
Appl. No.: 09/944,912
Filed: Aug. 31, 2001

U.S. Applications:

(63) Continuation of application No. 09/336,493, filed on Jun. 18, 1999, which is a continuation of application No. PCT/US97/24155, filed on Dec. 18, 1997.

(30) Foreign Application Priority Data

Dec. 18, 1996 (IL) ..... 119853
Mar. 24, 1997 (IL) ..... 120510

(51) Int. Cl.
*A61K 31/27* (2006.01)

(52) U.S. Cl. ..... 514/480; 514/481; 560/29; 560/32; 560/115; 560/136

(58) Field of Classification Search ..... 514/480, 514/481; 560/29, 32, 115, 136
See application file for complete search history.

(56) References Cited

U.S. PATENT DOCUMENTS

| | | | |
|---|---|---|---|
| 2,573,645 | A | 10/1951 | Kerwin et al. |
| 2,916,490 | A | 12/1959 | Schenck et al. |
| 2,982,783 | A | 5/1961 | Schenck et al. |
| 3,060,091 | A | 10/1962 | Witkin |
| 3,123,642 | A | 3/1964 | Temple et al. |
| 3,178,478 | A | 4/1965 | Huebner et al. |
| 3,201,470 | A | 8/1965 | Huebner et al. |
| 3,253,037 | A | 5/1966 | Huebner et al. |
| 3,308,157 | A | 3/1967 | Robertson et al. |
| 3,507,962 | A | 4/1970 | Taylor |
| 3,513,240 | A | 5/1970 | Bernardus et al. |
| 3,513,244 | A | 5/1970 | Gittos et al. |
| 3,637,740 | A | 1/1972 | Sarges |
| 3,704,323 | A | 11/1972 | Krapcho |
| 3,709,996 | A | 1/1973 | Gittos et al. |
| 3,751,420 | A | 8/1973 | Hauck et al. |
| 3,804,898 | A | 4/1974 | Panneman |
| 3,886,168 | A | 5/1975 | Himmele et al. |
| 3,991,207 | A | 11/1976 | Sarges et al. |
| 4,029,731 | A | 6/1977 | Sarges |
| 4,096,173 | A | 6/1978 | Molloy |
| 4,128,666 | A | 12/1978 | Bondinell et al. |
| 4,132,737 | A | 1/1979 | Molloy |
| 4,134,997 | A | 1/1979 | Cannon et al. |
| 4,172,093 | A | 10/1979 | Göransson-Dahlander et al. |
| 4,632,939 | A | 12/1986 | Beedle et al. |
| 4,638,001 | A | 1/1987 | Kuhla et al. |
| 4,788,130 | A | 11/1988 | Oshiro et al. |

(Continued)

FOREIGN PATENT DOCUMENTS

| | | | |
|---|---|---|---|
| EP | 0436492 | A2 | 10/1991 |
| EP | 0664291 | A1 | 10/1993 |
| EP | 0614888 | A1 | 2/1994 |
| EP | 0538134 | | 3/1997 |
| GB | 0852735 | | 11/1960 |
| GB | 1003686 | A | 9/1965 |
| JP | 3002155 | | 3/1991 |
| WO | WO9100724 | | 1/1991 |
| WO | WO9504027 | A1 | 2/1995 |
| WO | WO9511016 | A1 | 4/1995 |
| WO | WO9518617 | A1 | 7/1995 |
| WO | WO9602524 | | 2/1996 |

OTHER PUBLICATIONS

Armstrong et al., "Acylation Effects on Chiral Recognition of Racemic Amines and Alcohols by New Polar and Non–Polar Cyclodextrin Derivative Gas Chromatographic Phases", *J. Chromatography* (1990) 502: 154–159.

(Continued)

*Primary Examiner*—Samuel Barts
(74) *Attorney, Agent, or Firm*—John P. White, Esq.; Cooper & Dunham LLP

(57) ABSTRACT

This invention is directed to compounds of the following formula:

wherein when a is 0, b is 1 or 2; when a is 1, b is 1, m is from 0–3, X is O or S, Y is halogeno, $R_1$ is hydrogen $C_{1-4}$ alkyl, $R_2$ is hydrogen, $C_{1-4}$ alkyl, or optionally substituted propargyl and $R_3$ and $R_4$ are each independently hydrogen, $C_{1-6}$ alkyl, $C_{6-12}$ aryl, $C_{6-12}$ aralkyl each optionally substituted.

This invention is also directed to the use of these compounds for treating depression, Attention Deficit Disorder (ADD), Attention Deficit and Hyperactivity Disorder (ADHD), Tourette's Syndrome, Alzheimer's Disease and other dementia's such as senile dementia, dementia of the Parkinson's type, vascular dementia and Lewy body dementia.

This invention is further directed to a pharmaceutical composition comprising a therapeutically effective amount of the above-defined compounds and a pharmaceutically acceptable carrier.

58 Claims, 3 Drawing Sheets

U.S. PATENT DOCUMENTS

| | | | |
|---|---|---|---|
| 4,792,628 | A | 12/1988 | Oshiro et al. |
| 4,826,875 | A | 5/1989 | Chiesi |
| 4,833,273 | A | 5/1989 | Goel et al. |
| 4,873,241 | A | 10/1989 | Napier et al. |
| 4,948,807 | A | 8/1990 | Rosin et al. |
| 5,011,995 | A | 4/1991 | Pugin et al. |
| 5,071,875 | A | 12/1991 | Horn et al. |
| 5,118,704 | A | 6/1992 | Minaskanian et al. |
| 5,134,147 | A | 7/1992 | Peglion et al. |
| 5,153,225 | A | 10/1992 | Schohe et al. |
| 5,189,045 | A | 2/1993 | Peglion et al. |
| 5,196,583 | A | 3/1993 | Yamada et al. |
| 5,225,596 | A | 7/1993 | Carlsson et al. |
| 5,242,919 | A | 9/1993 | Oshiro et al. |
| 5,273,974 | A | 12/1993 | Goto et al. |
| 5,286,747 | A | 2/1994 | Arvidsson et al. |
| 5,378,729 | A | 1/1995 | Kohn et al. |
| 5,387,612 | A | 2/1995 | Youdim et al. |
| 5,389,687 | A | 2/1995 | Schaus et al. |
| 5,401,758 | A | 3/1995 | Atwal et al. |
| 5,453,446 | A | 9/1995 | Youdim et al. |
| 5,457,133 | A | 10/1995 | Youdim et al. |
| 5,486,541 | A | 1/1996 | Sterling et al. |
| 5,516,943 | A | 5/1996 | Gao et al. |
| 5,519,061 | A | 5/1996 | Youdim et al. |
| 5,532,415 | A | 7/1996 | Youdim et al. |
| 5,569,669 | A | 10/1996 | Guillaumet et al. |
| 5,576,353 | A | 11/1996 | Youdim et al. |
| 5,602,176 | A | 2/1997 | Enz |
| 5,646,188 | A | 7/1997 | Gilad et al. |
| 5,654,301 | A | 8/1997 | Kohn et al. |
| 5,708,018 | A | 1/1998 | Haadsma-Svensson et al. |
| 5,877,218 | A | 3/1999 | Herzig et al. |
| 5,914,349 | A | 6/1999 | Cohen et al. |
| 6,251,938 | B1 | 6/2001 | Chorev et al. |
| 6,303,650 | B1 | 10/2001 | Chorev et al. |
| 6,462,222 | B1 | 10/2002 | Chorev et al. |
| 2004/0010038 | A1 | 1/2004 | Blaugrund et al. |

OTHER PUBLICATIONS

Askin et al., "Highly Diastereoselective Alkylations of Chiral Amide Enolates: New Routes to Hydroxyethylene Dipeptide Isostere Inhibitors of HIV–1 Protease", *J. Org. Chem.* (1992) 57(10): 2771–2773.

Baker et al., "Synthesis of Decahydrocyclopentacyclo–octene Derivatives via Intramolecular Photocycloaddition of Butenolides and Reductive Cleavage", *J. Chem. Soc. Chem. Comm.* (1980) 23: 1011–1012.

Barton et al., "Reductive Formylation of Oximes; An Approach to the Synthesis of Vinyl Isonitriles", *Tetrahedron Letters* (1988) 29(27): 3343–3346.

Boar et al., "A Simple Synthesis of Enamides from Ketoximes", *J. Chem. Soc. Perkins I* (1975) 1237–1241.

Brettle et al., "Synthesis of Enamides", *J. Chem. Soc. Perkin Trans. I*, (1988) 2185–2193.

Burk et al., "A Three–Step Procedure for Asymmetric Catalytic Reductive Amidation of Ketones", *J. Org. Chem.* (1998) 63: 6084–6085.

Chorvat el al., "Acetycholine Release Enhancing Agents: Potential Therapeutics For Alzheimer's Disease", *Drugs of the Future* (1995) 20(11):1145–1162.

Cooper et al., "Alzheimer's Disease Drug Treatment", *J. Ger. Drug Ther.*, (1993) 8(2):5–18.

Cutler et al., "Muscarinic M1–Receptor Agonists", *CNS Drugs* (1995) 3(6):467–481.

Davis et al., "Tacrine", *The Lancet* (1995) 345:625–630.

Drefahl et al., "Amino Alcohols. I. Cis– and Trans–DL–1–amino–2–hydroxytetrahydronaphthalene and Cis– and Trans–DL–1–amino–2–hydroxyindan", *Chem. Abstracts* (1958) 52: 16417f.

Drefahl et al., "Amino Alcohols. X. Addition of Iodine Isocyanate to Unsymmetrical Olefins", *Chem. Abstracts* (1960) 54: 13078f.

Finberg and Youdim, "Modification of Blood Pressure and Nictitating Membrane Response to Sympathetic Amines by Selective Monoamine Oxidase Inhibitors, Types A and B, in the Cat", *Brit. J. Pharmacol.* (1985) 85(2): 541–546.

Fink et al., "Imino 1,2,3,4–Tetrahydrocyclopent[B]indole Carbamates as Dual Inhibitors of Acetylcholinesterase and Monoamine Oxidase", *Bioorganic & Medicinal Chemistry Letters* (1996) 6(6): 625–630.

Fuller et al., "Inhibition in vitro of Norepinephrine N–methyltransferase by 2–Aminotetralins, Analogs of Phenylethylamines with Rigid Conformation", *Biochem. Pharmacol.*, (1976) 26: 446–447.

Gabryel et al., "Nootropics: Pharmacological Properties and Therapeutic Use", *Pol. J. Pharmacol.* (1994) 46:383–394.

Ghislandi et al., "Scissione Ottica E Configurazione Dell'1–Aminobenzociclobutene E Dell'1–Aminoindano", *Boll. Chim. Farm.* (1976) 115: 489–500.

Harvey, "The Pharmacology of Galanthamine and its Analogues", *Pharmac. Ther.* (1995) 68(1):113–128.

Heikkila et al., "Prevention of MPTP–Induced Neurotoxicity by AGN–1133 and AGN–1135, Selective Inhibitors of Monoamine Oxidase–B", *Eur. J. Pharmacol.* (1985) 116: 313–317.

Hori et al., "N–containing Diphenylethylamine Derivatives and Acid Adducts", Japan Kokai Tokyo Koho JP 54–132559, Oct. 15, 1979, Database CAPLUS on STN®, *Chemical Abstracts Service*, (Columbus, Ohio), Accession No. 1980:180807, abstract.

Horn et al., "Steric Requirements for Catecholamine Uptake by Rat Brain Synaptosomes: Studies with Rigid Analogs of Amphetamine", *J. Pharmacol. Exp. Ther.* (1972) 180: 523–530.

Huebner, "1–(N–Methyl–N–propargylamino)indans and Related Compounds", *Chem. Abstracts* (1964) 61:3046a.

Kabins et al., "Potential Applications for Monoamine Oxidase B Inhibitors", *Dementia* (1990) 1: 323–348.

Kametani et al., "Studies on the Syntheses of Heterocyclic Compounds. CLIX. The Reaction of 2–Nitro–1–indanone Oxime with Formalin and Hydrochloric Acid", *Chem. Pharm. Bull.* (1966) 14(12): 1408–1413.

Knapp et al., "A 30–Week Randomized Controlled Trial of High–Dose Tacrine in Patients with Alzheimer's Disease", *J.A.M.A.* (1994) 271(13) 985–991.

Laso et al., "A New Selective Reduction of Nitroalkenes into Enamides", *Tetrahedron Letters* (1996) 37(10): 1605–1608.

Martin et al., "Potential Anti–Parkinson Drugs Designed by Receptor Mapping", *J. Med. Chem.* (1973) 16(2): 147–150.

Martin et al., "Discriminant Analysis of the Relationship Between Physical Properties and the Inhibition of Monoamine Oxidase by Aminotetralins and Aminoindans", *J. Med. Chem.* (1974) 17(4): 409–413.

Mouna et al., "Enantioselective Acetylation of Primary Amines by *Cylindrocarpon Radicicola", Bioorg. & Med. Chem. Letters*. (1993) 3(4): 681–684.

Nakanishi et al., "Preparation of Enamides via Reductive Acylation of N–Acetoxyimino Compounds by Use of $Fe_3(CO)_{12}$" *Chemistry Letters* (1987) 2167–2168.

O'Malley et al., "Synthesis and Biological Evaluation of Combined Acetyl Cholinesterase (AChE) and Monoamine Oxidase (MAO) Inhibitors", 205$^{th}$ ACS Mtg., 1993 (MEDI), abstract 78.
Oshiro et al., "Novel Cerebroprotective Agents with Central Nervous System Stimulating Activity. 1. Synthesis and Pharmacology of 1–Amino–7–hydroxyindan Derivatives", *J. Med. Chem.* (1991) 34(7): 2004–2013.
Palermo et al., "Combined Acetylcholinesterase (AChE) and Reversible Monoamine Oxidase (MAO) Inhibition as a Potential Therapeutic Approach For Senile Dementia of the Alzheimer Type (SDAT)", 205$^{th}$ ACS Mtg., 1993 (MEDI), abstract 77.
Riederer and Youdim, "Monoamine Oxidase Activity and Monoamine Metabolism in Brains of Parkinson's Patients Treated with l–Deprenyl", *J. Neurochem.* (1986) 46(5): 1359–1365.
Ruschig et al., "Preparation of 17–hydroxy–20–keto Steroids from 17(20)–en–20–acetamino Steroids", *Chem. Ber.* (1955) 88(6):883–894.
Singh et al., "Antimalarials. 7–Chloro–4–(substituted amino)quinolines", *J. Med. Chem.* (1971) 14(4): 283–286.
Sramek et al., "Safety/Tolerability Trial of SDZ ENA 713 in Patients with Probable Alzheimer's Disease", *Life Sciences* (1996) 58(15):1201–1207.
Tariot et al. "Treatment of Alzheimer's Disease: Glimmers of Hope", *Chem. Ind.* (1993) 20:801–3, 806–7.
Tekes et al., "Effect of MAO Inhibitors on the Uptake and Metabolism of Dopamine in Rat and Human Brain", *Pol. J. Pharmacol. Pharm.* (1988) 40: 653–658.
Teranishi et al., "Facile Synthesis of 6–Hydroxyindole and 6–Methoxyindole via Regioselective Friedel–Crafts Acylation and Baeyer–Villiger Oxidation", *Synthesis* (1994) 1018–1020.
Terni et al., "Preparation of (aminoalkyl) phenyl morpholinoalkylcarbamates and analogs as cholinesterase inhibitors", WO 96/02524, Feb. 1, 1996, Database CAPLUS on STN®, *Chemical Abstracts Service* (Columbus, Ohio), Accession No. 1996:340192, abstract.
Top et al., "N–Alkylation of Nitriles with Tricarbonylchromium Complexes of Benzyl and Related Alcohols as Synthetic Intermediates. Further Development of the Ritter Reactions", *J.C.S. Chem. Comm.* (1979) 224–225.
Weinstock, "The Pharmacotherapy of Alzheimer's Disease Based on the Cholinergic Hypothesis: an Update", *Neurodegeneration* (1995) 4:349–356.
Youdim et al., "Monamine Oxidase" in *Handbook of Experimental Pharmacology*, v. 90/I (Trendelenburg and Weiner, eds., Springer–Verlag, London: 1988) Chpt. 3, 119–192.
Zheng et al., "Asymmetric Synthesis of Amino Acid Derivatives via an Electophilic Amination of Chiral Amide Cuprates with Li t–Butyl–N–Tosyloxycarbamate", *Tetrahedron Letters* (1997) 38(16): 2817–2820.
Zhu et al., "Asymmetric Rh–Catalyzed Hydrogenation of Enamides with a Chiral 1,4–Bisphosphine Bearing Diphenylphosphino Groups", *J. Org. Chem.* (1998) 63: 9590–9593.
"Agent for Cognition Disorders Acetylcholinesterase Inhibitor", *Drugs of the Future*, E–2020 (1991) 16(1): 16–18.
"Cognition Enhancer Acetylcholinesterase Inhibitor" *Drugs of the Future*, E–2020 (1995) 20(1): 77–78.
"Cognition Enhancer Acetylcholinesterase Inhibitor", *Drugs of the Future*, TAK–147 (1995) 20(3): 248–250.
*The Merck Index* (Windholz et al., eds., Merck & Co., Inc., Rahway, NJ, 10th ed., 1983) 149, 248–249.
*The Merck Manual of Diagnosis and Therapy*, (Berkow et al., eds., Merck Sharp & Dohme Research Laboratories, 15$^{th}$ ed., 1987) 1030–1033.
*The Merck Manual of Diagnosis and Therapy*, (Berkow et al., eds., Merck Sharp & Dohme Research Laboratories, 15$^{th}$ ed., 1987) 1054–1055.
The Parkinson Study Group, "Effect of Deprenyl on the Progression of Disability in Early Parkinson's Disease" *New Eng. J. Med.* (1989) 321(20: 1364–1371.
The Parkinson Study Group, "Effects of Tocopherol and Deprenyl on the Progression of Disability in Early Parkinson's Disease" *New Eng. J. Med.* (1993) 328(3): 176–183.

AMINOINDAN DERIVATIVES

Matter enclosed in heavy brackets [ ] appears in the original patent but forms no part of this reissue specification; matter printed in italics indicates the additions made by reissue.

This application is a continuation of U.S. Ser. No. 09/336,493, filed Jun. 18, 1999, a continuation of PCT International Application No. PCT/US97/24155, filed Dec. 18, 1997, designating the United States of America and claiming priority of Israeli Patent Application Nos. 119853, filed Dec. 18, 1996 and 120510, filed Mar. 24, 1997, the contents of which are hereby incorporated by reference.

FIELD OF INVENTION

The present invention relates to novel compounds, pharmaceutical compositions containing said compounds and their use in the treatment of various CNS disorders.

BACKGROUND OF THE INVENTION

Dementia exists in several forms including static dementia, Alzheimer's-type dementia, senile dementia, presenile dementia and progressive dementia. One of the common pathological features of several types of dementia is the lack of the neurotransmitter acetylcholine. This has led to the development of acetylcholine esterase inhibitors for use in the treatment of dementias such as the compound tacrine. A summary of the different approaches to and progress made in the treatment of Alzheimer's Disease may be found in Drugs of the Future (1995) 20(11): 1145–1162.

Recently, compounds that in addition to inhibiting acetylcholine esterase, possess inhibitory activity against monoamine oxidase type A (MAO-A) have been developed. The perceived benefit of having the anti-MAO-A activity is stated to be an anti-depressant effect (European Patent Publication Nos. 614,888 and 664,291).

U.S. Pat. Nos. 5,387,133, 5,453,446, 5,457,133 and 5,519,061 all disclose that the compound (R)-N-propargyl-1-aminoindan, a highly selective monoamine oxidase type B (MAO-B) inhibitor is effective in the treatment of dementias of the Alzheimer type and memory disorders. There is no indication given therein that the compound might have acetylcholine esterase inhibitory activity. Furthermore, the compound is only very weakly active as a MAO-A inhibitor.

PCT International Publication No. WO95/18617 discloses various aminoindan derivatives that are active in a variety of CNS disorders including dementias of the Alzheimer type. There is no indication given therein that any of the compounds disclosed might have acetylcholine esterase inhibitory activity.

SUMMARY OF THE INVENTION

The present invention relates to compounds of formula I

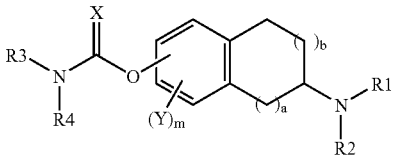

wherein when a is 0; b is 1 or 2; when a is 1, b is 1; m is from 0 to 3; X is C or S; Y is halogeno; $R_1$ is hydrogen or $C_{1-4}$ alkyl; $R_2$ is hydrogen, $C_{1-4}$ alkyl or optionally substituted propargyl; and $R_3$ and $R_4$ are each independently hydrogen, $C_{1-8}$ alkyl, $C_{6-12}$ aryl, $C_{6-12}$ aralkyl or $C_{6-12}$ cycloalkyl optionally substituted.

The invention relates to the compounds themselves, pharmaceutical compositions containing said compounds and their use in the treatment of depression, Attention Deficit Disorder (ADD), Attention Deficit and Hyperactivity Disorder (ADHD), Tourette's Syndrome, Alzheimer's Disease and other dementias such as senile dementia, presenile dementia, progressive dementia, dementia of the Parkinson's type, vascular dementia and Lewy body dementia.

A further aspect of the present invention relates to the use of the compounds of formula I in the treatment of neurotraumatic disorder. As used herein the term "neurotraumatic disorder" is meant to include damage caused to the nervous system (both central and peripheral) by virtue of ischemic damage such as that which occurs in stroke, hypoxia or anoxia, neurodegenerative diseases, Parkinson's Disease, Alzheimer's Disease, Huntington's Disease, neurotoxic injury, head trauma injury, spinal trauma injury, peripheral neuropathy or any form of nerve damage.

An additional aspect of the present invention relates to the use of the compounds of formula I in the treatment of memory disorder or depression.

The present invention relates to the racemic compounds themselves and optically active enantiomers thereof.

DETAILED DESCRIPTION OF THE INVENTION

Figure 1:
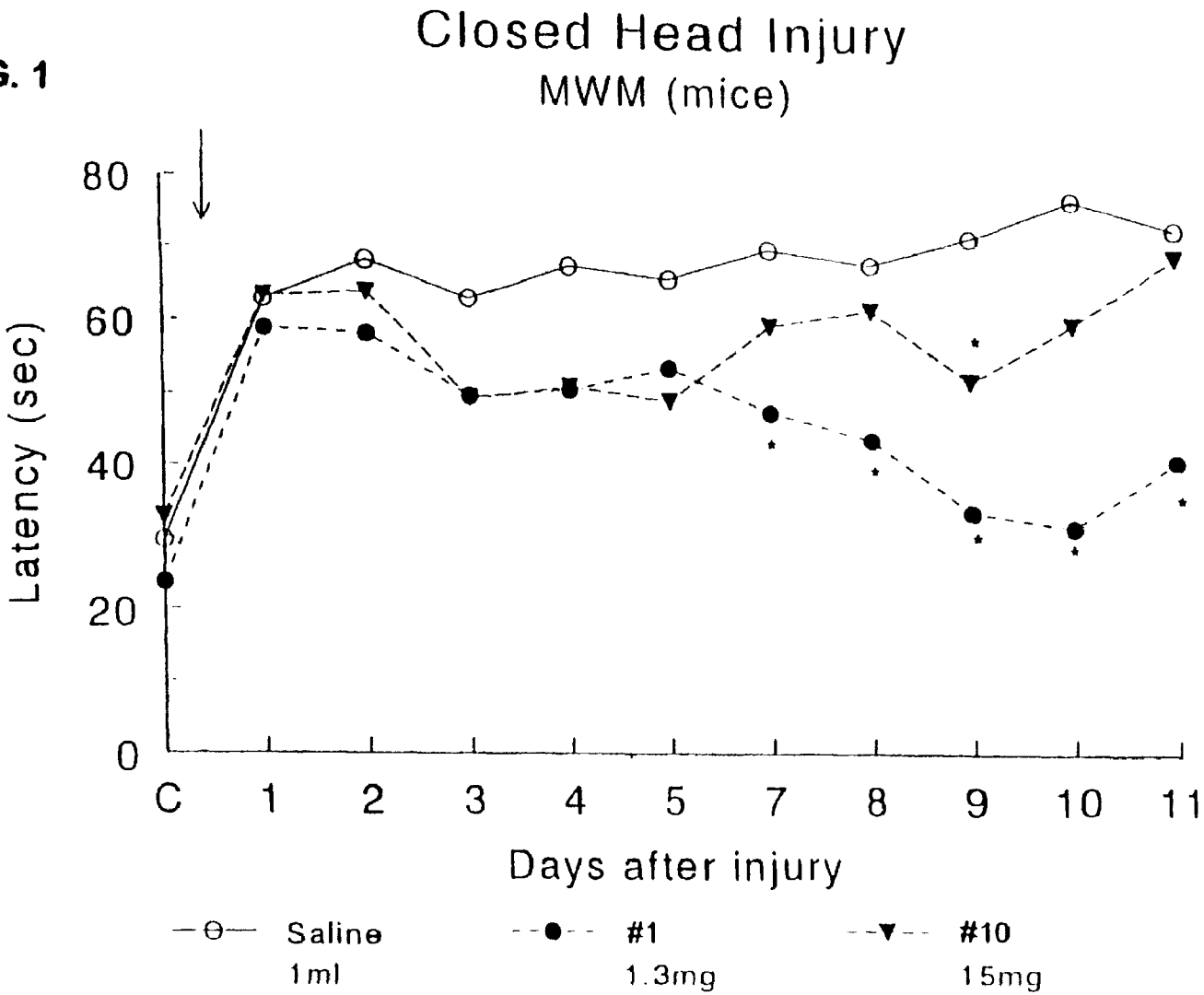
FIG. 1 shows the reduction in latency for mice after closed head injury in the Morris Water Maze Test after treatment with compound 1, compound 10 or Saline (Control) The arrow shows the time off closed head injury.

The present invention is directed to compound of Formula I:

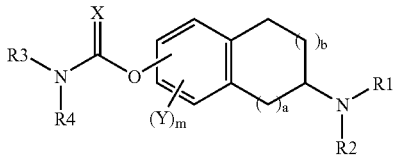

wherein when a is 0, b is 1 or 2; when a is 1, b is :, m is from 0–3, X is O or S; Y is halogen; $R_1$ is hydrogen or $C_{1-4}$ alkyl; $R_2$ is hydrogen, $C_{1-4}$ alkyl, or optionally substituted propargyl and $R_3$ and $R_4$ are each independently hydrogen, $C_{1-6}$ alkyl, $C_{6-11}$ aryl, $C_{6-11}$; aralkyl or $C_{6-11}$ cycloalkyl each optionally substituted.

In an embodiment of the present invention, a is 0 and b is 1. In another embodiment of the present invention, a is 0, b is 1, and X is O.

In an embodiment of the present invention, X is O. In an additional embodiment of the present invention, X is S.

In an embodiment of the present invention, $R_1$ is selected from the group consisting of hydrogen, methyl, ethyl or optionally substituted propargyl.

In another embodiment of the present invention, $R_1$ is propargyl.

In a further embodiment of the present invention, the compound is selected from the group consisting of: (rac) 6-(N-methyl, N-ethyl-carbanyloxy)-N'-propargyl-1-aminoindan HCl; (rac) 6-(N,N-dimethyl, carbanyloxy)-N'-methyl-N'-propargyl-1-aminoindan HCl; (rac) 6-(N-methyl, N-ethyl-carbamyloxy)-N'-propargyl-1-aminotetralin HCl; (rac)6-(N,N-dimethyl-thiocarbamyloxy)-1-aminoindan HCl; (rac)6-(N-propyl-carbamyloxy)-N'-propargyl-1-aminoindan HCl; (rac)5-chloro-6-(N-methyl, N-propyl-carbamyloxy)-N'-propargyl-1-aminoindan HCl; (S)-6-(N-methyl, N-propyl-carbamyloxy)-N'-propargyl-1-aminoindan HCl; and (R)-6-(N-methyl, N-ethyl-carbamyloxy)-N'-propargyl-1-aminoindan hemi-(L)-tartrate.

In a further embodiment of the present invention, $R_1$ is hydrogen, methyl or ethyl and $R_2$ is hydrogen, methyl, ethyl or optionally substituted propargyl. In a further embodiment of the present invention, the propargyl group is substituted with a $C_{1-4}$ alkyl group on the methylene group ($R_6$ in Scheme I)

According to the present invention, the term "halogeno" is used to refer to fluoro, chloro, bromo, or iodo.

In an embodiment of the present invention, when m is greater than 1 each Y may be the same or different.

In an additional embodiment of the present invention, the group $OC(X)NR_3R_4$ is on the 4, 6 or 7 position of the indan ring counting from the amino substituted carbon.

In another embodiment of the present invention, at least one of $R_3$ and $R_4$ is methyl and the other is hydrogen, methyl, ethyl, propyl, butyl, hexyl, phenyl, benzyl or cyclohexyl.

In the practice of this invention, pharmaceutically acceptable salts include, but are not limited to, the esylate, mesylate, maleate, fumarate, tartrate, hemi-tartarate, hydrochloride, hydrobromide, p-toluenesulfonate, benzoate, acetate, phosphate and sulfate salts.

The subject invention further provides a pharmaceutical composition which comprises a therapeutically effective amount of a compound of formula I or a pharmaceutically acceptable salt thereof and a pharmaceutically acceptable carrier. The "therapeutically effective amount" of a compound of formula I or a pharmaceutically acceptable salt thereof may be determined according to methods well known to those skilled in the art, indications of such amounts are given below.

These compositions may be prepared as medicaments go be administered orally, parenterally, rectally, or transdermally.

Suitable forms for oral administration include tablets, compressed or coated pills, dragees, sachets, hard or soft gelatin capsules, sublingual tablets, syrups and suspensions. In one embodiment, the pharmaceutically acceptable carrier is a solid and the pharmaceutical composition is a tablet. The therapeutically effective amount may be an amount from about 0.5 mg to about 2000 mg, preferably from about 1 mg to about 1000 mg.

In an alternative embodiment, the pharmaceutically acceptable carrier is a liquid and the pharmaceutical composition is an injectable solution. The therapeutically effective amount may be an amount from about 0.5 mg to about 2000 mg, preferably from about 1 mg to about 1000 mg. The volume administered may be an amount between 0.5 and 10 ml.

In a further alternative embodiment, the carrier is a gel and the pharmaceutical composition is a suppository. For parenteral administration the invention provides ampoules or vials that include an aqueous or non-aqueous solution or emulsion. For rectal administration there are provided suppositories with hydrophilic or hydrophobic vehicles. For topical application as ointments and transdermal delivery there are provided suitable delivery systems as known in the art. For oral or suppository formulations, 0.5–2000 mg per dosage unit and preferably 1–1000 mg per dosage unit.

These compositions may be used alone to treat the above-listed disorders, or alternatively, for example, in the case of Alzheimer's Disease, they may be used as an adjunct to the conventional treatments such as haloperidol, tacrine or deprenyl.

The invention will be better understood from the Experimental Details which follow. However, one skilled in the art will readily appreciate that the specific methods and results discussed are merely illustrative of the invention as described more fully in the claims which follow thereafter.

EXAMPLES

Compounds of general formula I may be prepared, as shown in Scheme I, from the corresponding carbamoyl derivatives of aminoindan III by reacting the latter with propargyl compounds bearing an appropriate leaving group at the 3-position, e.g. a halide group, mesylate, tosylate, etc., under basic cenditions provided by an inorganic base, e.g. $K_2CO_3$, NaOH, or an organic base e.g. a tertiary amine, in a polar organic solvent, e.g. $CH_3CN$, DMF, etc., at 15–40° C., preferably at 20–25° C., for a period of time in the range of 5–48 hours, preferably 20–30 hours. The products, obtained after a suitable work-up and purification, are in the form of free bases. Preferably these are converted into their pharmaceutically acceptable salts, e.g. HCl, mesylate, hemi-tartarate, etc.

As shown in Scheme I, compounds of general formula III may be prepared by Boc deprotection of compounds of general formula IV. In turn, compounds of general formula IV may be prepared by carbamylating a compound of general formula V in a conventional manner, e.g. by reacting the compound of formula V with an appropriate carbamoyl halogenide or by an alkylisocyanate. Finally, compounds of general formula V may be prepared by Boc protection of the appropriate hydroxy amines, by methods known to those skilled in the art. N,N-dialkyl aminoindan derivatives may be prepared as shown on in Scheme I by the direct carbamylation of the corresponding N,N-dialkyl-hydroxy-aminoindan or by alkylation of a compound of formula III.

Although Scheme I shows the preparation of carbamoyl derivatives the same process and description above is relevant to the preparation of the thiocarbamates of the present invention.

Starting Materials 6- and 7-Hydroxy-1-aminoindans may be prepared by demethylation of the respective 6- and 7-methoxy-1-aminoindans. The latter may be obtained from the corresponding 1-indanones, either by their conversion to the oximes, followed by reduction, or by their reductive amination ($NaCNBH_3$ and $NH_4OAc$)[2].

6-Hydroxy aminoindan may also be prepared from aminoindan via a regioselective Friedel—Crafts acylation of a suitably N-protected aminoindan, followed by a Baeyer—Williger oxidation and finally hydrolysis[5]. 6-hydroxy-(R)-1-aminoindan may thus be prepared by the method described in the Example below and Scheme II, wherein "R" is optionally substituted alkyl.

N-Methyl-6-hydroxy-1-aminoindan was prepared by demethylation of 6-methoxy-N-methyl-1-aminoindan, which was prepared from 6-methoxy-1-aminoindan by reductive alkylation (e.g. ethyl formate, followed by $LiAlH_4$ reduction), or alternatively, by reductive amination ($MeNH_2$, HCl, $NaCNBH_3$) of 6-methoxy-1-indanone[2]. N-ethyl-6-hydroxy-1-aminoindan was obtained by acetylation of 6-hydroxy-1-aminoindan ($Ac_2O$, KOH), followed by reduction ($LiAH_4$). N,N-Dimethyl-6-hydroxy-1-aminoindan was prepared by demethylation of the corresponding 6-methoxy analogue, which was prepared by reductive alkylation (formaldehyde, formic acid) of 6-methoxy-1-aminoindan. 4-Hydroxy-1-aminoindan may be prepared from 4-hydroxy indanone by converting the latter to the oxime, followed by reduction[1]. 4-Hydroxy indanone may be prepared from dihydrocoumarin.[3]

7-Hydroxy-1-aminotetralin and 7-hydroxy-2-aminotetralin were prepared by demethylation of the corresponding 7-methoxy analogues. The latter were prepared by reductive amination (as above) of the corresponding 7-methoxy-1- and 2-tetralones.

7-Methoxy-2-tetralone was prepared from 2,7-dimethoxytetralin according to Copinga,et al[4].

Preparation of 6-Hydroxy-(R)-1-aminoindan (As Shown in Scheme II)

N-Trifluoroacetyl-(R)-1-aminoindan

To a cooled (0–5° C.) solution of trifluoroacetic anhydride (194.6 g, 0.926 mol) in toluene (680 ml) was added dropwise a solution of (R)-1-aminoindan (base) (113.32 g 0.85 mol) in toluene (50 ml) and stirred under ice-cooling for 3½ hours. A solution of KOH (67.25 g, 1.2 mol) in water (1000 ml) was then added, under cooling. The reaction mixture was stirred for further 2 hours at room temperature and filtered. The solid was collected by filtration, washed with water (680 ml) and dried in vacuo at 60° C. to give 152 g (78%) of a white solid, mp:153–154° C. The solution was evaporated in vacuum and the crystals were filtered and washed with water. The solid was dried in vacuo at 60° C. The second crop (25 g) was crystallized from a mixture of hexane and ethyl acetate to give 189 (9%) of a white solid, mp:153–154° C. The total yield was 170 g (87%).

6-Chloroacetyl-N-trifluoroacetyl-(R)-1-aminoindan

To a suspension of $AlCl_3$ (89.2 g, 0.67 mol) in 1,2-dichloroethane (600 ml) was added chloroacetyl chloride (55.7 ml, 78.9 g, 0.7 mol) dropwise at 0–5° C. under nitrogen for 20 minutes and it was then left to warm up to 20–25° C. To this mixture was added N-trifluoroacetyl-(R)-1-aminoindan (34.4 g, 0.15 mol) for 3 hours at 20–25° C. The resulting mixture was then stirred for an additional 30 minutes and poured into a mixture of ice-cold water (1.5 l) and 1,2-dichloroethane (1l). The mixture was stirred for 5 minutes and the layers were separated. The aqueous layer was extracted with 1,2-dichloroethane (2×750 ml). The combined organic layers were washed with water (2×900 ml) and 5% aqueous $NaHCO_3$ solution (3×900 ml). The organic layer was dried ($Na_2SO_4$) and the solvent was removed under reduced pressure to give a solid, which was recrystallized from ethanol to give 15 g (48%) of a white solid mp: 166–167° C.

6-Chloroacetoxyl-N-trifluoroacetyl-(R)-1-aminoindan

6-Choroacetyl-N-trifluoroacetyl-(R)-1-aminoindan (30.57 g, 0.1 mol) was dissolved in anhydrous dichloromethane (210 ml) and 3-chloroperoxybenzoic acid (70%, 44.87 g, 0.26 mol) was added all at once. The suspension was cooled to 0° C. and trifluoroacetic acid (11.4 g, 0.1 mol) was added dropwise for 5–10 minutes. The reaction flask was protected from light and the mixture was stirred for 3–5 days at room temperature. The reaction mixture was poured into water (300 ml.). The mixture was neutralized with ammonium hydroxide solution. The layers were separated. The aqueous layer was extracted with dichloromethane (200 ml). The combined organic layers were dried ($Na_2SO_4$) and the solvent was removed under reduced pressure to give a solid, which was recrystallized from ethanol to give 15 g (48%) of a white solid mp: 169–170° C.

6-Hydroxy-(R)-1-aminoindan

A suspension of 6-chloroacetoxy-N-trifluoroacetyl-(R)-1-aminoindan (25.4, 0.11 mol) and $K_2CO_3$ (38.0 g, 0.275 mol) in a mixture of methanol (275 ml) and water (175 ml) was stirred at 70° C. for 1.5 hours. Methanol was removed in vacuo, and the aqueous phase was neutralized with 10% hydrochloric acid. The mixture was filtered and the solid was washed with water. The mother liquor was evaporated under reduced pressure to a small volume. The suspension was neutralized, filtered and the brown solids were crystallized from methanol (twice) to give 7.0 g (43%) of a white solid mp:200–203° C.

Preparation of the corresponding S-enantiomer may be carried out in the same manner using (S)-1-aminoindan as the starting material.

Resolution of Enantiomers

The R- and S-enantiomers of each compound may be obtained by optical resolution of the corresponding racemic mixtures. Such a resolution can be accomplished by any conventional resolution method well known to a person skilled in the art, such as those described in U.S. Pat. No. 4,833,273, issued May 23, 1989 (Goel) and in J. Jacques, A. Collet and S. Wilen, "Enantiomers, Racemates and Resolutions," Wiley, N.Y. (1981). For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallization to isolate the diastereomeric salt of the desired enantiomer.

Alternatively, selected starting materials, intermediates or end products may be resolved into their respective enantiomers by the method described in PCT International Application Publication No. WO/96US/21640, wherein the compound to be resolved is first converted into its N-benzyl derivative. The N-benzyl derivative is then resolved using either R or S-mandelic acid. The resolved product is converted to its base and reduced under acidic conditions to provide the desired enantiomer. Preferably, the starting material is resolved prior to Boc protection and carbamylation.

The R and S enantiomers of the starting materials may also be prepared from R and S enantiomers c: aminoindan via a regioselective Friedel—Crafts acylation so a suitably N-protected optical isomer of aminoindan, followed by a Baeyer-Williger oxidation and finally hydrolysis[5], thus obviating the need for optical resolution.

REFERENCES

1. Y. Oshiro, et al, *J. Med. Chem.* 34: 2004 (1991);
2. R. F. Borch, et al, J. Am. Chem. Soc. 93:, 2897 (1971);
3. J. G. Cannon, et al, J. Med. Chem. 28: 515 (1985);
4. S. C. Copinga, et al, J. Med. Chem. 36: 2891 (1993); and
5. K. Teranishi et al, Synthesis 1018 (1994).

Preparation of Compounds of the Invention as Shown in Scheme I

A: Boc—protection and carbamylation

1. Boc Protection 6-hydroxy N-Boc aminoindan

A solution of 6-hydroxy aminoindan (16 g, 107 mmol), di-t-butyl dicarbonate (23.8 g, 109.2 mmol) and $Et_3N$ (16.74 ml, 120 mmol) in THF (375 ml) was stirred at room temperature (RT) for 20 hrs. The reaction mixture was evaporated to dryness under reduced pressure, and the residue was dissolved in $CH_2Cl_2$ (200 ml), washed with water (200 ml), dried over $Na_2SO_4$ and evaporated to dryness under reduced pressure. The crude product was purified by column chromatography (hexane/EtOAc 2:1) to give 23 g of a solid (86%).

2. Carbamylation 6-(N-Me, N-Et carbamyloxy) N-Boc aminoindan

To a stirred and ice-cooled solution of N-Boc 6-hydroxy aminoindan (7.5 g, 30 mmol) in acetonitrile (75 ml) was added N-Me,N-Et carbamoyl chloride (6.3 g, 51.8 mmol), followed by a dropwise addition of NaH (60% in oil, 1.56 g, 39 mmol). The reaction mixture was stirred for 2 hrs at RT under argon. After evaporation of the solvent in-vacuo, water (100 ml) was added, and extracted with ether (3×100 ml). The organic phase was washed with dilute NaOH (pH 10–11), dried and evaporated to dryness in-vacuo. Purification by column chromatography (hexane:EtOAc 2:1) afforded 7.8 g (77%) of an oil.

In this manner the intermediates in Tables 1 and 2 were prepared. In Table 1 and all further Tables the heading "position" refers to the ring position of the carbamyl group unless otherwise indicate

TABLE 1

N-Boc protected carbomyloxy aminoindans

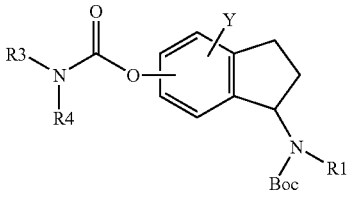

| position | Y | R1 | R3 | R4 | yield (%) |
|---|---|---|---|---|---|
| 6- | H | H | Me | Me | 92 |
| 6- | H | H | Me | Pr | 95 |
| 6- | H | H | Me | Et | 77 |
| 7- | H | H | Me | Me | 92 |
| 7- | H | H | Me | Et | 83 |
| 7- | H | H | Me | Pr | 95 |
| 6- | H | Et | Me | Me | 76 |
| 6- | H | Me | Me | Me | 92 |
| 7- | H | Me | Me | Me | 78 |
| 6- | H | Me | Me | Pr | 80 |
| 6- | H | H | Me | n-hexyl | 98 |
| 4- | H | H | Me | Me | 85 |
| 4- | H | H | Me | Et | 87 |
| 6- | H | H | Me | Et | 89 |
| 6- | H | H | Me | cyclohexyl | 98 |
| 6- | H | H | Me | p-OMe-phenyl | 97 |
| 6- | H | H | Me | phenyl | 93 |
| 6- | H | H | Me | $CH_2$-phenyl | 83 |
| 6- | 5-Cl | H | Me | Et | 88 |
| 6- | 5-Cl | H | Me | Pr | 97 |
| 6- | H | H | Me | Bu | 99 |
| 6- | H | H | Et | Bu | 93 |
| 6- | H | H | Et | cyclohexyl | 94 |

TABLE 2

N-Boc protected carbomyloxy tetralins

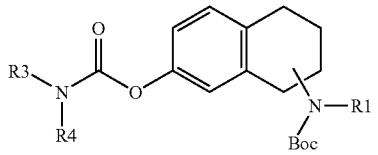

| position of amine | R1 | R3 | R4 | yield (%) |
|---|---|---|---|---|
| 2- | H | Me | Me | 85 |
| 2- | H | Me | Et | 79 |
| 1- | H | Me | Me | 85 |
| 1- | H | Me | Et | 98 |

B: Boc—Deprotection 6-(N-Me,N-Et Carbamyloxy) aminoindan HCl (Compound 3)

6-(N-Me,N-Et Carbamyloxy) N-Boc aminoindan (7.8 g, 23.3 mmol) was dissolved in dioxane (80 ml), and a 20% solution of gas. HCl in dioxane (80 ml) was added. After 2 hr stirring at RT the solvent was evaporated in-vacuo and the residue was treated with dry ether (200 ml) and the mixture stirred at RT for 4 hrs and filtered, to give 6.15 g (0.7 mmol, 97%) of 6-(N-Me, N-Et carbamyloxy) aminoindan hydrochloride.

In this manner the following compounds of general formula I as shown in Tables 3, 3a and 4 were prepared. Spectral data relating to these compounds is given in Tables 7, 7a and 8.

TABLE 3

Carbamyloxy aminoindan HCl salts

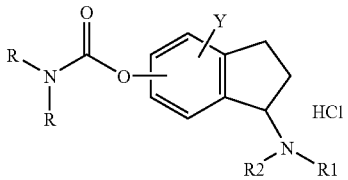

| # | position | R1, R2 | R3 | R4 | cryst/ slurry solvent | mp(° C.) | yield (%) |
|---|---|---|---|---|---|---|---|
| 1 | 6- | H, H | Me | Me | $Et_2O$ | 156–8 | 93 |
| 2 | 6- | H, H | Me | Pr | $Et_2O$ | 165–7 | 27 |
| 3 | 6- | H, H | Me | Et | $Et_2O$ | 150–2 | 50 |
| 4 | 7- | H, H | Me | Me | $Et_2O$ | 156–60 | 93 |
| 5 | 7- | H, H | Me | Et | $Et_2O$ | 185–7 | 55 |
| 6 | 7- | H, H | Me | Pr | $Et_2O$ | 153–5 | 33 |
| 7 | 6- | H, Et | Me | Me | $Et_2O$ | 172–4 | 91 |
| 8 | 6- | H, Me | Me | Me | $Et_2O$ | 178–80 | 88 |
| 9 | 7- | H, Me | Me | Me | dioxane | 169–71 | 98 |
| 10 | 6- | H, Me | Me | Et | $Et_2O$ | 172–4 | 87 |
| 11 | 6- | H, Me | Me | Pr | $Et_2O$ | 165–7 | 98 |
| 12 | 6- | Me, Me | Me | Me | $Et_2O$ | 164–6 | 62 |
| 13 | 4- | H, H | Me | Me | $Et_2O$ | 198–200 | 90 |
| 14 | 4- | H, H | Me | Et | $Et_2O$ | 183–5 | 92 |
| 15 | 6- | H, H | Me | n-hexyl | dioxane | 111–12 | 78 |
| 16* | 6- | H, H | Me | Et | $Et_2O$ | 197–8 | 89 |
| 17 | 6- | H, H | Me | cyclo hexyl | $Et_2O$ | 207–8 | 86 |
| 18** | 6- | H, H | Me | Et | $Et_2O$ | 202–4 | 84 |
| 48 | 6- | H, H | H | Et | MeOH/ EtOAc | 191–2 | 74 |

TABLE 3-continued

Carbamyloxy aminoindan HCl salts

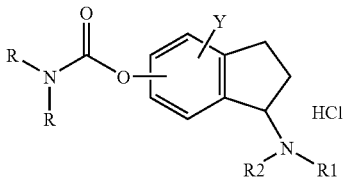

| # | position | R1, R2 | R3 | R4 | cryst/slurry solvent | mp(° C.) | yield (%) |
|---|---|---|---|---|---|---|---|
| 49 | 6- | H, H | H | Pr | MeOH/EtOAc | 171–3 | 67 |
| 50 | 6- | H, H | Me | p-OMe-Phenyl | iPrOH | 225–7 | 92 |
| 51 | 6- | H, H | Me | $CH_2$—Ph | $Et_2O$ | | 78 |
| 52* | 6- | H, H | Me | Me | $Et_2O$ | | 83 |
| 53** | 6- | H, H | Me | Me | $Et_2O$ | | 81 |
| 88 | 6- | H, H | Me | Ph | $Et_2O$ | | 96 |
| 66*** | 6- | H, H | Me | Et | $Et_2O$ | 116–9 | 92 |
| 67*** | 6- | H, H | Me | Pr | $Et_2O$ | 181–3 | 86 |
| 80 | 6- | H, H | Me | Bu | $Et_2O$ | | 54 |
| 84 | 6- | H, H | Et | cyclo-hexyl | $Et_2O$ | 196–8 | 89 |

*R < nantiomer
**S-cnantiomer
***5-chloro

TABLE 3a

Thiocarbamyloxy aminoindan HCl salts

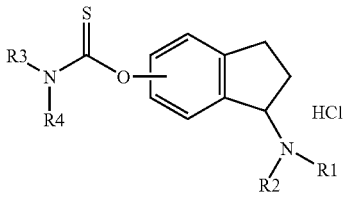

| # | position | R1, R2 | R3 | R4 | cryst/slurry solvent | mp(° C.) | yield (%) |
|---|---|---|---|---|---|---|---|
| 44 | 6- | H, H | Me | Me | MeOH/EtO | 244–5 | 55 |
| 45 | 6- | H, H | Me | Et | MeOH/EtOAc | 236–8 | 58 |

TABLE 4

Carbamyloxy aminotetralin HCl salts

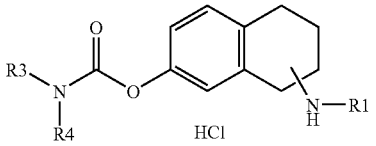

| # | position of amine | R1 | R3 | R4 | cryst/slurry solvent | mp(° C.) | yield (%) |
|---|---|---|---|---|---|---|---|
| 19 | 2- | H | Me | Me | ether | a) | 96 |
| 20 | 2- | H | Me | Et | ether | a) | 98 |

TABLE 4-continued

Carbamyloxy aminotetralin HCl salts

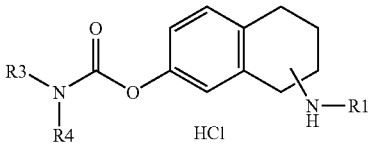

| # | position of amine | R1 | R3 | R4 | cryst/slurry solvent | mp(° C.) | yield (%) |
|---|---|---|---|---|---|---|---|
| 21 | 1- | H | Me | Me | ether | 196–8 | 99 |
| 22 | 1- | H | Me | Et | ether | 166–8 | 85 |

a) wide melting range; compound is a hemi-hydrate

C: Propargylation and salt formation

The compounds prepared in Step B may be optionally propargylated to provide further compounds of general formula I.

6-(N-Me, N-Et carbamyloxy) N-propargyl aminoindan, HCl (Compound 25)

To a stirred mixture of 6-(N-Me, N-Et carbamyloxy) aminoindan. HCl (5.2 g, 19.2 mmol), potassium carbonate (5.31 g, 38.4 mmol) in acetonitrile (250 ml), was added a solution of propargyl bromide (2.06 g, 17.28 mmol) in acetonitrile (10 ml). The reaction mixture was stirred at RT under nitrogen for 25 hrs, and filtered. The filtrate was evaporated to dryness in-vacuo and the residue was purified by column chromatography (EtOAc) to give 3.6 g (13.2 mmol, 69%) of the free base as a yellow oil.

The free base was dissolved in dry ether (150 ml) and HCl/ether (15 ml) was added. The mixture was stirred at RT for 1 hr, filtered and the solid was recrystallized from iPrOH/ether to give 3.5 g (11.3 mmol, 59%) of the title compound as a white solid.

6-(N,N-Dimethylcarbamyloxy)-N-propargyl aminoindan mesylate (Compound 24)

To a stirred mixture of 6-(N,N-dimethylcarbamyloxy) aminoindan HCl (1.88 g, 7.33 mmol), $K_2CO_3$ (2.03 g, 14.66 mmol) and acetonitrile (70 ml) was added a solution of propargyl bromide (0.79 g, 6.6 mmol) in $CH_3CN$ (5 ml) dropwise over 5 min, under nitrogen. The mixture was stirred under $N_2$ for 24 hrs, filtered and the solvent was removed at reduced pressure. The residue was taken up into water (150 ml) and toluene (150 ml). This mixture was stirred while adjusting the pH of the aqueous layer to 3.75 by the addition of 20% aq. HCl. The aqueous layer was separated and extracted with toluene (2×100 ml) and brought carefully to pH 7.5 by the addition of 10% aq. NaOH solution. It was then extracted with toluene (100 ml+4×70 ml). The combined toluene layers were dried ($Na_2SO_4$), filtered and the solvent was removed under reduced pressure to give 1.06 g (62%) of a yellow oil.

To a stirred solution of the free base (1.65 g, 6.4 mmol) in anh. ether (60 ml) was added dropwise a solution of methanesulfonic acid (0.7 g, 7.29 mmol) in ether (10 ml). The resulting suspension was stirred at 25° C. for 30 man and then allowed to settle for an additional 30 min. The ether was then decanted off, and the residue was dried under vacuum. It was then recrystallized from iPrOH/ether to give 2.05 g of a white solid (90.3%).

In this manner the following compounds of general formula I as shown in Tables 5, 5a and 6 were prepared. Analytical data relating to these compounds is given in Tables 9, 9a and 10.

TABLE 5

Carbamyloxy-N-propargyl aminoindans

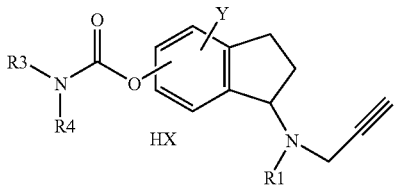

| # | X | position | R1 | R3 | R4 | cryst/slurry solvent | mp (° C.) | yield (%) |
|---|---|---|---|---|---|---|---|---|
| 23 | Cl | 6- | H | Me | Me | iPrOH/$Et_2O$ | 180–2 | 52 |
| 24 | mesylate | 6- | H | Me | Me | iPrOH/$Et_2O$ | 147–9 | 60 |
| 25 | Cl | 6- | H | Me | Et | iPrOH/$Et_2O$ | 194–6 | 59 |
| 26 | Cl | 6- | H | Me | Pr | iPrOH/$Et_2O$ | 183–5 | 46 |
| 27 | Cl | 7- | H | Me | Me | iPrOH/$Et_2O$ | 219–20 | 65 |
| 28 | Cl | 7- | H | Me | Pr | iPrOH/$Et_2O$ | 185–6 | 53 |
| 29 | Cl | 6- | Me | Me | Me | iPrOH/$Et_2O$ | 199–201 | 55 |
| 30 | Cl | 6- | Me | Me | Et | $Et_2O$ | 196–8 | 47 |
| 31 | Cl | 6- | Et | Me | Me | iPrOH/$Et_2O$ | 212–3 | 71 |
| 32 | Cl | 7- | Me | Me | Me | iPrOH/$Et_2O$ | 169–71 | 63 |
| 33 | Cl | 7- | H | Me | Et | iPrOH/$Et_2O$ | 208–9 | 64 |
| 34 | Cl | 4- | H | Me | Me | $Et_2O$ | 196–8 | 85 |
| 35 | Cl | 4- | H | Me | Et | $Et_2O$ | 183–5 | 85 |
| 36 | Cl | 6- | H | Me | n-hexyl | iPrOH/$Et_2O$ | 106–8 | 53 |
| 37* | Cl | 6- | H | Me | Et | $Et_2O$ | 159–6 | 88 |
| 38 | Cl | 6- | H | Me | cyclohexyl | $Et_2O$ | 174–5 | 55 |
| 39** | Cl | 6- | H | Me | Et | $Et_2O$ | 160–2 | 61 |
| 54* | mesylate | 6- | H | Me | Me | $Et_2O$ | 139–41 | 54 |
| 55** | mesylate | 6- | H | Me | Me | $Et_2O$ | 138–40 | 52 |
| 56 | Cl | 6- | H | H | Et | iPrOH/$Et_2O$ | 175–7 | 38 |
| 57 | Cl | 6- | H | H | Pr | iPrOH/$Et_2O$ | 165–7 | 48 |
| 58 | mesylate | 6- | H | Me | Et | $Et_2O$ | 92–4 | 64 |
| 59** | mesylate | 6- | H | Me | Et | iPrOH/$Et_2O$ | | 72 |
| 60 | mesylate | 6- | H | Me | Et | $Et_2O$ | 121–3 | 87 |
| 61 | Cl | 6- | H | Me | p-OMe-Ph | $Et_2O$ | 172–4 | 84 |
| 62 | Cl | 6- | H | Me | Ph | $Et_2O$ | 182–4 | 61 |
| 63 | Cl | 6- | H | Me | $CH_2Ph$ | $Et_2O$ | 188–90 | 58 |
| 64*** | Cl | 6- | H | Me | Me | iPrOH/$Et_2O$ | 195–7 | 55 |
| 65*** | Cl | 6- | H | Me | Et | iPrOH/$Et_2O$ | 188–90 | 51 |
| 68**** | fumarate | 6- | H | Me | Et | iPrOH | 146–8 | 48 |
| 69* | fumarate | 6- | H | Me | Et | iPrOH | 115–7 | 35 |
| 70 | crylate | 6- | H | Me | Et | EtOAc | 109–11 | 60 |
| 71**** | Cl | 6- | H | Me | Et | $Et_2O$ | 161–3 | 55 |
| 72**** | Cl | 6- | H | Me | Pr | $Et_2O$ | 164–6 | 58 |
| 73** | fumarate | 6- | H | Me | Et | iPrOH | 114–6 | 81 |
| 74** | crylate | 6- | H | Me | Et | EtOAc | 95–7 | 82 |
| 75** | [½D-tartrale] *½D-tartrate* | 6- | H | Me | Et | iPrOH | 143–5 | 44 |
| 76* | [½L-tarate] *½L-tartrate* | 6- | H | Me | Et | iPrOH | 143–5 | 41 |
| 77* | crylate | 6- | H | Me | Et | EtOAc | 106–8 | 93 |
| 78* | Cl | 6- | H | Me | Pr | $Et_2O$ | 126–8 | 89 |
| 79* | Cl | 6- | H | Me | Pr | $Et_2O$ | 135–7 | 33 |
| 81 | Cl | 6- | H | Me | Bu | $Et_2O$ | 168–70 | 63 |
| 83 | Cl | 6- | H | Et | Bu | $Et_2O$ | 148–50 | 42 |
| 85 | Cl | 6- | H | Et | cyclohexyl | $Et_2O$ | 178–80 | 56 |
| 86* | Cl | 6- | H | Me | Bu | $Et_2O$ | 86–8 | 51 |
| 87** | Cl | 6- | H | Me | Bu | $Et_2O$ | 88–9 | 52 |

*R-enantiomer

**S-enantiomer

***substituted propargyl derivatives, $R_n$ in Scheme 1 is methyl

****Y: 5-Cl

TABLE 5a

Thiocarbamyloxy-N-propargyl aminoindans

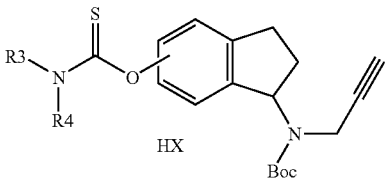

| # | X | position | R1 | R3 | R4 | cryst/slurry solvent | mp (° C.) | yield (%) |
|---|---|---|---|---|---|---|---|---|
| 46 | Cl | 6- | H | Me | Me | $Et_2O$ | 152–4 | 53 |
| 47 | Cl | 6- | H | Me | Et | $Et_2O$ | 193–5 | 54 |

TABLE 6

N-Propargyl aminotetralins

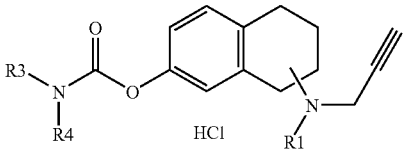

| # | position of amine | R1 | R3 | R4 | cryst/slurry solvent | mp (° C.) | yield (%) |
|---|---|---|---|---|---|---|---|
| 40 | 2- | H | Me | Me | $MeOH/Et_2O$ | 206–8 | 66 |
| 41 | 2- | H | Me | Et | $iPrOH/Et_2O$ | 208–9 | 65 |
| 42 | 1- | H | Me | Me | ether | 207–9 | 57 |
| 43 | 1- | H | Me | Et | ether | 201–3 | 42 |

TABLE 7

Analytical Data of Compounds of the Invention shown in Table 3

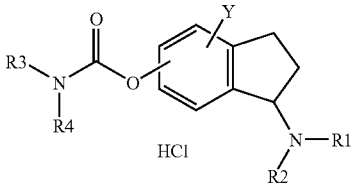

| # | NMR$_1$ aryl | index | R1, R2 | R3, R4 | IR | MS (MH*) | elem. anal. (C, H, N) |
|---|---|---|---|---|---|---|---|
| 1 | 7.38, 7.20<br>7.10 | 4.85, 3.10<br>2.96, 2.63<br>2.14 | | 3.10, 2.96 | 3446, 2943<br>1711, 1487<br>1393, 1240 | 221 | calc: 56.14, 6.62, 10.90<br>found: 55.90, 6.67, 10.89 |
| 2 | 7.40, 7.21<br>7.10 | 4.80, 3.10<br>2.95, 2.65<br>2.15 | | 3.43, 3.27<br>3.10, 2.95<br>1.70, 1.63<br>0.94, 0.90 | 2970, 2863<br>1735, 1608<br>1396, 1241 | 249 | calc: 59.05, 7.38, 9.84<br>found: 58.75, 7.33, 9.86 |
| 2a (½ $H_2O$ | 7.40, 7.21<br>7.10 | 4.80, 3.10<br>2.95, 2.65<br>2.15 | | 3.43, 3.27<br>3.10, 2.95<br>1.70, 1.63<br>0.94, 0.90 | 2970, 2863<br>1735, 1608<br>1396, 1241 | 249 | calc: 57.23, 7.55, 9.54<br>found: 57.54, 7.29, 9.45 |
| 4 | 7.47, 7.36<br>7.09 | 4.91, 3.25<br>3.07, 2.60<br>2.25 | | 3.18, 3.03 | 2950, 1701<br>1504, 1396<br>1234, 1177 | | |
| 5 | 7.44, 7.29<br>7.02 | 4.88, 3.20<br>3.14, 2.55<br>2.23 | | 3.55, 3.39<br>3.14, 2.99<br>1.26, 1.18 | 3446, 2920<br>1710, 1472<br>1403, 1235 | 235 | calc: 57.70, 7.25, 10.35<br>found: 57.38, 6.97, 10.32 |
| 6 | 7.45, 7.30<br>7.02 | 4.86, 3.20<br>3.04, 2.55<br>2.23 | | 3.50, 3.32<br>3.13, 2.98<br>1.70, 1.63<br>0.94, 0.90 | 3448, 2923<br>1710, 1485<br>1226, 1154 | 249 | calc: 59.05, 7.43, 9.84<br>found: 58.78, 7.47, 9.91 |
| 7 | 7.45, 7.29<br>7.17 | 4.83, 3.17<br>3.02, 2.65 | 3.20, 1.33 | 3.15, 3.0 | 2948, 2766<br>2680, 1725<br>1485, 1386 | 249 | calc: 59.05, 7.38, 9.84<br>found: 57.75, 7.40, 9.65 |
| 8 | 7.43, 7.27<br>7.17 | 4.75, 3.14<br>3.03, 2.60<br>2.30 | 2.73 | 3.13, 2.97 | 2950, 2722<br>1720, 1390<br>1160 | 235 | calc: 57.70, 7.02, 10.35<br>found: 56.83, 7.09, 10.27 |
| 9 | 7.52, 7.37<br>7.10 | 4.83, 3.27<br>3.10, 2.55<br>2.38 | 2.74 | 3.19, 3.04 | 2963, 2710<br>1715, 1579<br>1472, 1389 | 235 | calc: 57.70, 7.02, 10.35<br>found: 57.46, 6.73, 10.36 |
| 10 | 7.44, 7.29<br>7.15 | 4.80, 3.15<br>3.03, 2.62<br>2.30 | 2.74 | 3.55, 3.35<br>3.12, 2.98<br>1.25, 1.18 | 2950, 2705<br>1720, 1450<br>1402 | | calc: 59.08, 7.38, 9.84<br>found: 58.74, 7.51, 9.72 |

TABLE 7-continued

Analytical Data of Compounds of the Invention shown in Table 3

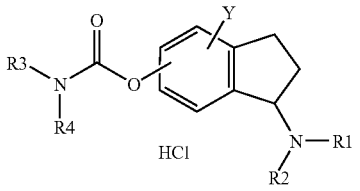

| | NMR[1] | | | | | MS | elem. anal. |
|---|---|---|---|---|---|---|---|
| # | aryl | index | R1, R2 | R3, R4 | IR | (MH*) | (C, H, N) |
| 11 | 7.42, 7.25<br>7.14 | 4.75, 3.15<br>3.10, 2.60<br>2.28 | 2.72 | 3.45, 3.30<br>3.10, 2.95<br>1.65, 0.94<br>0.88 | 2963, 2723<br>1715, 1465<br>1404, 1234 | | calc: 60.33, 7.70, 9.38<br>found: 60.32, 7.75, 9.42 |
| 12 | 7.43, 7.27<br>7.17 | 4.96, 3.12<br>3.05, 2.55<br>2.42 | 2.75 | 3.10, 2.96 | 3480, 1718<br>1475, 1390<br>1237, 1174 | 249 | calc: 59.05, 7.38, 9.84<br>found: 58.75, 7.41, 9.84 |
| 13[11] | 7.53, 7.29<br>7.08 | 4.71, 2.95,<br>2.74, 2.45,<br>2.0 | 8.75 | 3.04, 2.9 | | 221 | |
| 14[11] | 7.53, 7.3,<br>7.08 | 4.71, 2.95,<br>2.73, 2.48,<br>2.0 | 8.7 | 3.41, 3.3,<br>3/01, 2.89,<br>1.18, 1.07 | | 235 | |
| 15 | 7.35, 7.23<br>7.01 | 4.83, 3.3<br>2.6, 2.16 | | 3.1, 3.06<br>2.95, 2.91<br>1.6, 1.29<br>0.85 | 2930, 1720<br>1471, 1405<br>1248 | 291 | calc: 62.47, 8.33, 8.57<br>found: 62.54, 8.30, 8.61 |
| 16 | 7.42, 7.22<br>7.12 | 4.87, 3.16<br>3.01, 2.65<br>2.17 | | 3.53, 3.39<br>3.92, 2.99<br>1.26, 1.17 | | 235 | |
| 17 | 7.42, 7.22<br>7.11 | 4.87, 3.15<br>2.95, 2.65<br>2.17 | | 4.10, 3.85<br>3.00, 2.85<br>1.90- 1.40<br>1.34, 1.13 | | 289 | calc: 62.85, 7.76, 8.63<br>found: 62.55, 7.81, 8.33 |
| 3 | 7.43, 7.20<br>7.12 | 4.86, 3.15<br>3.02, 2.64<br>2.18 | | 3.51, 3.38<br>3.10, 2.95<br>1.25, 1.15 | | 235 | calc: 55.70, 7.25, 10.35<br>found: 57.44, 7.06, 10.38 |
| 18 | 7.43, 7.20<br>7.12 | 4.86, 3.15<br>3.02, 2.64<br>2.18 | | 3.51, 3.38<br>3.10, 2.95<br>1.25, 1.35 | | 235 | calc: 55.70, 7.25, 10.35<br>found: 57.44, 7.06, 10.38 |
| 48 | 7.41, 7.24<br>7.13 | 4.87, 3.13<br>3 0, 2.65<br>2.17 | | 3.23, 1.17 | | 221 | calc: 56.13, 6.68, 10.91<br>found: 56.00, 6.66, 10.81 |
| 49 | 7.41, 7.24<br>7.13 | 4.87, 3.12<br>2.98, 2.65<br>2.17 | | 3.17, 1.56<br>0.94 | | 235 | calc: 57.67, 7.07, 10.35<br>found: 57.32, 7.13, 10.31 |
| 50 | 7.37, 7.16<br>7.03 | 4.80, 3.10<br>2.96, 2.61<br>2.15 | | 7.40- 7.0<br>3.82, 3.43<br>3.29 | | | calc: 61.98, 6.02, 8.03<br>found: 61.16, 6.07, 7.77 |
| 66 | 7.57, 7.39 | 4.91, 3.18<br>3.05, 2.71,<br>2.25 | | 3.61, 3.43<br>3.20, 3.03<br>1.33, 1.23 | | 269<br>271 | calc: 50.41, 6.02, 9.05<br>found: 50.46, 6.11, 8.77 |
| 67 | 7.55, 7.36 | 4.89, 3.14<br>3.02, 2.68<br>2.20 | | 3.52, 3.36<br>3.18, 3.02<br>1.77, 1.67<br>0.99, 0.93 | | 283<br>285 | calc: 52.67, 6.32, 8.78<br>found: 52.67, 6.28, 8.48 |

[1] $D_2O$, unless otherwise specified

[11] DMSO-$d_6$

TABLE 7a

Analytical Data of Compounds of the Invention shown in Table 3a

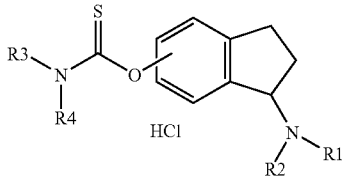

| # | NMR($D_2O$) aryl | indan | R1, R2 | R3, R4 | IR | MS ($MH^+$) | elem. anal. (C, H, N, S) |
|---|---|---|---|---|---|---|---|
| 44 | 7.45, 7.20, 7.11 | 4.87, 3.15, 3.05, 2.65, 2.20 | | 3.44, 3.36 | 2933, 1714, 1599, 1536, 1488, 1392 | | calc: 52.83, 628, 10.27, 11.75<br>found: 51.11, 6.48, 10.23, 12.16 |
| 45 | 7.45, 7.20, 7.11 | 4.75, 3.10, 2.97, 2.65, 2.20 | | 3.88, 3.79 3.39, 3.32, 1.28, 1.25 | 2934, 1719, 1594, 1522, 1497, 1402 | | calc: 51.22, 6.94, 9.19, 10.52<br>found: 51.04, 7.30, 9.31, 11.24 |

TABLE 8

Analytical Data of Compounds of the Invention shown in Table 4

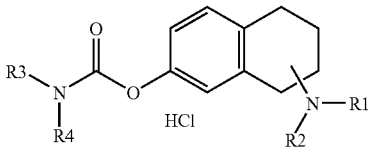

| # | NMR[2] aryl | cyclohex. | R1, R2 | R3, R4 | IR | MS ($MH^+$ | elem. anal. (C, H, N) |
|---|---|---|---|---|---|---|---|
| 19 (½$H_2O$) | 7.22, 6.95 | 3.69, 3.22 2.93, 2.87 2.22, 1.92 | | 3.12, 2.97 | 3484, 2930 2362, 1699 1612, 1500 1391 | 235 | calc: 55.81, 7.20, 10.02<br>found: 55.29, 6.93, 9.71 |
| 20 (½$H_2O$) | 7.20, 6.94 | 3.70, 3.19 2.90, 2.23 1.90 | | 3.48, 3.35 3.08, 2.94 1.20, 1.12 | | 249 | calc: 57.23, 7.55, 9.54<br>found: 57.50, 7.53, 9.54 |
| 21 | 7.28, 7.11, 7.06 | 3.10, 2.96 2.77, 2.16 2.05, 1.88 | | 3.10, 2.96 | | 235 | calc: 57.70, 7.02, 10.35<br>found: 56.97, 6.93, 10.06 |
| 22 | 7.29, 7.13, 7.07 | 4.57, 2.88 2.79, 2.15 2.05, 1.90 | | 3.52, 3.37 3.10, 2.97 1.25, 1.17 | | 249 | calc: 59.05, 7.38, 9.84<br>found: 58.91, 7.18, 9.99 |

[2]$D_2O$, unless otherwise specified

TABLE 9

Analytical Data of Compounds of the Invention shown in Table 5

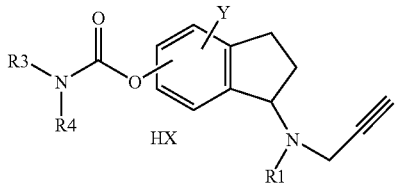

| # | NMR[3] aryl | indan | R1 | proparg | R3, R4 | IR | MS ($MH^+$) | elem. anal. (C, H, N) |
|---|---|---|---|---|---|---|---|---|
| 23 | 7.46, 7.30 7.18 | 5.01, 3.20 3.15, 2.65 2.36 | | 4.0, 3.16 | 3.15, 3.0 | | 259 | calc: 61.12, 6.50, 9.51<br>found: 60.93, 6.38, 9.47 |

TABLE 9-continued
Analytical Data of Compounds of the Invention shown in Table 5
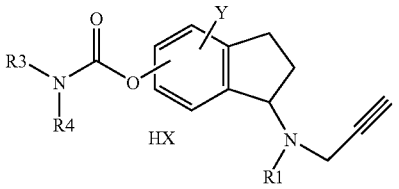
| | NMR[3] | | | | | | MS | elem. anal. |
|---|---|---|---|---|---|---|---|---|
| # | aryl | indan | R1 | proparg | R3, R4 | IR | (MH+) | (C, H, N) |
| 24 | 7.46, 7.30 7.18 | 5.01, 3.20 3.15, 2.65 2.36 | | 4.0, 3.16 | 3.15, 3.02 | 1711, 1482, 1439, 1394, 1192, 1170 | 259 | calc: 54.22, 6.26, 7.91 found: 53.92, 6.28, 7.84 |
| 25 | 7.42, 7.27 7.15 | 4.97, 3.16 3.0, 2.62 2.32 | | 3.97, 3.02 | 3.52, 3.36 3.10, 2.97, 1.24, 1.15 | 1728, 1435, 1403, 1242, 1166 | 273 | calc: 62.23, 6.86, 9.57 found: 62.42, 6.84, 8.94 |
| 25[a] | 7.50, 7.32 7.10 | 4.78, 3.10 2.85, 2.45 2.28 | | 3.91, 3.74 | 3.43, 3.32 3.03, 2.90 1.20, 1.10 | 1728, 1435, 1403, 1242, 1166 | 273 | calc: 62.23, 6.86, 9.57 found: 62.42, 6.84, 8.94 |
| 26 | 7.45, 7.30 7.17 | 5.0, 3.16 3.04, 2.65 2.33 | | 4.0, 3.03 | 3.48, 3.32 3.12, 2.98 1.72, 1.63 0.96, 0.92 | 1725, 1465, 1429, 1403, 1232, 1165 | 287 | calc: 63.25, 7.18, 8.68 found: 63.13, 7.28, 8.93 |
| 27 | 7.52, 7.38 7.10 | 5.05, 3.26 3.07, 2.56 2.40 | | 3.90, 3.21 | 3.12, 3.03 | 3200, 1722, 1567, 1434, 1408, 1238 | 259 | calc: 61.12, 6.50, 9.51 found: 61.01, 6.46, 9.64 |
| 28 | 7.52, 7.37 7.07 | 5.02, 3.27 3.09, 2.55 2.38 | | 3.98, 3.10 | 3.65, 3.42 3.18, 3.02 1.75, 0.98 0.93 | 3200, 1727, 1566, 1468, 1438, 1406, 1222 | 287 | calc: 63.25, 7.18, 8.68 found: 63.06, 7.30, 8.37 |
| 29 | 7.44, 7.30 7.19 | 5.20, 3.15 3.03, 2.57, 2.44 | 2.80 | 4.01, 3.13 | 3.12, 2.97 | 1729, 1388, 1234, 1165 | 273 | calc: 62.33, 6.80, 9.07 found: 61.97, 6.80, 8.78 |
| 31 | 7.48, 7.30 7.23 | 5.34, 3.20 3.08, 2.65 2.50 | 3.36, 1.37 | 4.05, 3.12 | 3.16, 3.01 | 3180, 1723, 1490, 1440, 1389, 1230, 1160 | 287 | calc: 63.25, 7.18, 8.68 found: 63.42, 7.09, 8.71 |
| 32 | 7.56, 7.39 7.15 | 5.30, 3.28 3.09, 2.55 | 2.78 | 4.12, 3.23 | 3.20, 3.02 | 1712, 1472, 1392, 1238, 1171 | 273 | calc: 62.23, 6.86, 9.07 found: 62.05, 6.81, 8.87 |
| 33 | 7.46, 7.32 7.03 | 4.96, 2.50 2.33 | | 3.92, 3.04 | 3.13, 2.96 1.24, 1.15 | 1719, 1426, 1404, 1233, 1154 | 273 | calc: 62.23, 6.86, 9.07 found: 62.19, 6.77, 9.08 |
| 34 | 7.48, 7.23 | 5.07, 3.08 2.95, 2.65 2.35 | | 4.05, 3.07 | 3.29, 3.03 | 3238, 2907 2769, 2635 1714, 1470 1392, 1240 | 259 | calc: found: |
| 35 | 7.48, 7.23 | 5.07, 3.08 2.95, 2.65 2.35 | | 4.05, 3.07 | 3.56, 3.41 3.15, 3.01 1.29, 1.21 | 3197, 2934 2565, 2431 1707, 1445 1403, 1236 | 273 | calc: found: |
| 36 | 7.45, 7.28 7.15 | 4.98, 3.16 3.03, 2.63 2.33 | | 3.98, 3.04 | 3.49, 3.35 3.11, 2.97 1.66, 1.33 0.88 | | | calc: 65.83, 8.01, 7.68 found: 65.65, 8.11, 7.82 |
| 37 | 7.44, 7.29 7.18 | 4.98, 3.15 3.01, 2.63 2.31 | | 3.98, 3.03 | 3.53, 3.38 3.12, 2.98 1.25, 1.16 | 3275, 2754 1719, 1445 1395, 1303 | 273 | calc: 62.23, 6.86, 9.07 found: 62.30, 6.94, 9.09 |
| 38 | 7.44, 7.27 7.16 | 4.98, 3.14 3.00, 2.64 2.33 | | 3.98, 3.04 | 4.09, 3.85 3.01, 2.88 1.90–1.45 1.35, 1.14 | 3227, 2936 2612, 2128 1713, 1584 1440, 1401 | 327 | calc: 66.19, 7.50, 7.72 found: 65.90, 7.63, 7.55 |
| 39 | 7.46, 7.30 7.19 | 4.97, 3.17 3.04, 2.64 2.32 | | 3.97, 3.03 | 3.54, 3.39 3.13, 3.0 1.27, 1.19 | 3275, 2933 2758, 1720 1442, 1396 1303 | 273 | calc: 62.23, 6.86, 9.07 found: 62.27, 6.95, 9.03 |
| 54 | 7.46, 7.30 7.19 | 5.00, 3.17 3.05, 2.64 2.33 | | 3.99, 3.05 | 3.15, 3.0 | 1711, 1482 1438, 1395 1192, 1169 | 259 | calc: 54.17, 6.20, 7.90 found: 54.18, 6.27, 7.78 |
| 55 | 7.46, 7.30 7.19 | 5.00, 3.17 3.05, 264 2.33 | | 3.99, 3.05 | 3.15, 3.0 | 1711, 1482 1438, 1395 1192, 1169 | 259 | calc: 54.17, 6.20, 7.90 found: 54.07, 6.25, 7.88 |

TABLE 9-continued
Analytical Data of Compounds of the Invention shown in Table 5
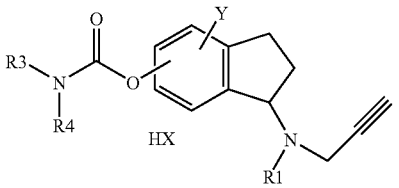
| # | NMR[3] aryl | indan | R1 | proparg | R3, R4 | IR | MS (MH+) | elem. anal. (C, H, N) |
|---|---|---|---|---|---|---|---|---|
| 56 | 7.46, 7.32 7.20 | 4.99, 3.17 3.04, 2.65 2.33 | | 3.99, 3.05 | 3.27, 1.20 | | 259 | calc: 61.12, 6.50, 9.51 found: 60.87, 6.47, 9.34 |
| 57 | 7.47, 7.32 7.20 | 4.99, 3.18 3.05, 2.65 2.34 | | 3.99, 3.06 | 3.20, 1.61 0.98 | | 273 | calc: 62.23, 6.86, 9.07 found: 61.60, 6.93, 9.04 |
| 58 | 7.47, 7.32 7.22 | 5.01, 3.20 3.08, 267 2.36 | | 4.01, 3.07 | 3.56, 3.41 3.14, 3.01 1.29, 1.21 | | 273 | calc: 55.43, 6.52, 7.60 found: 55.08, 6.52, 7.31 |
| 59 | 7.47, 7.32 7.22 | 5.01, 3.20 3.08, 2.67 2.36 | | 4.01, 3.07 | 3.56, 3.41 3.14, 3.01 1.29, 1.21 | | 273 | calc: found: |
| 60 | 7.47, 7.32 7.22 | 5.01, 3.20 3.08, 2.67 2.36 | | 4.01, 3.07 | 3.56, 3.41 3.14, 3.01 1.29, 1.21 | | 273 | calc: 55.43, 6.52, 7.60 found: 55.21, 6.64, 7.40 |
| 61 | 7.40–7.0 | 4.96, 3.10 2.97, 2.57 2.30 | | 3.96, 3.90 3.03 | 7.40–7.0 3.81 | | 351 | calc: 65.20, 5.95, 7.24 found: 64.72, 6.04, 6.81 |
| 62 | 7.60–7.10 | 4.96, 3.15 3.00, 2.61 2.34 | | 3.98, 3.07 | 7.60–7.10 3.42 | | 321 | calc: 67.32, 5.89, 7.85 found: 67.22, 6.00, 7.54 |
| 63 | 7.55–7.10 | 4.97, 3.17, 3.00, 2.64, 2.36, 2.36 | | 3.99, 3.07 | 7.55–7.10 4.73, 4.59 3.14, 3.05 | | 335 | calc: 67.47, 6.20, 7.55 found: 67.75, 6.32, 7.47 |
| 64 | 7.48, 7.35 7.21 | 5.16, 5.12 3.20, 3.05 2.70, 2.35 | | 4.44, 4.27 3.17, 1.68 1.63 | 3.17, 3.03 | | 273 | calc: 62.23, 6.86, 9.07 found: 62.22, 6.86, 8.96 |
| 65 | 7.44, 7.36, 7.27, 7.19 | 5.15, 5.09 3.20, 3.02 2.65, 2.32 | | 4.43, 4.25 3.25, 3.17 1.67, 1.61 | 3.55, 3.39 3.13, 3.00 1.27, 1.19 | | | calc: 63.25, 7.18, 8.68 found: 63.15, 7.15, 8.31 |
| 71 | 7.60, 7.44 | 5.02, 3.20, 3.06, 2.68, 2.36 | | 4.02, 3.07 | 3.60, 3.43, 3.20, 3.02, 1.33, 1.23 | | 307 309 | calc: 55.98, 5.87, 8.16 found: 55.72, 5.88, 8.11 |
| 72 | 7.59, 7.44 | 5.01, 3.20, 3.06, 2.68, 2.38 | | 4.03, 3.07 | 3.53, 3.36, 3.20, 3.02, 1.79, 1.68, 1.01, 0.95 | | 321 323 | calc: 57.15, 6.21, 7.84 found: 57.05, 6.21, 7.81 |
| 76 | 7.47, 7.31, 7.20 | 5.00, 3.20, 3.06, 2.66, 2.35 | | 4.00, 3.07 | 3.56, 3.40, 3.16, 3.00, 1.28, 1.20 | 3286, 2972, 1724, 1637, 1400, 1308, 1233 | 273 | calc: 62.17, 6.62, 8.05 found: 62.31, 6.66, 7.94 |
| 81 | 7.48, 7.31, 7.20 | 5.00, 3.20, 3.07, 2.66, 2.35 | | 4.01, 3.07 | 3.53, 3.38, 3.14, 3.01, 1.65, 1.39, 0.97 | | | calc: 64.19, 7.42, 8.32 found: 63.99, 7.42, 8.04 |
| 83 | 7.47, 7.31, 7.19 | 5.00, 3.19, 3.04, 2.66, 2.34 | | 4.01, 3.07 | 3.52, 3.38, 1.68, 1.40, 1.29, 1.22, 0.98 | | 315 | calc: 65.04, 7.70, 7.98 found: 64.75, 7.72, 7.94 |
| 85 | 7.47, 7.31, 7.19 | 5.00, 3.19, 3.02, 2.63, 2.34 | | 4.01, 3.07 1.85, 1.66, 1.23 | 3.84, 3.42 | | 341 | calc: 66.33, 7.70, 7.43 found: 66.75, 7.69, 7.36 |
[2]$D_2O$, unless otherwise specified
[a]DMSO-$d_d$ TABLE 9a Analytical Data of Compounds of the Invention shown in Table 5a

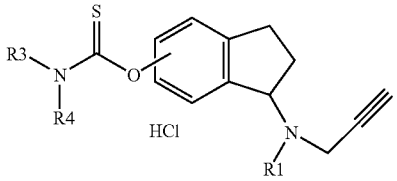

| # | NMR ($D_2O$) aryl | indan | propargyl | R3, R4 | IR | MS ($MH^+$) | elem. anal. (C, H, N, S) |
|---|---|---|---|---|---|---|---|
| 46 | 7.48, 7.29, 7.16 | 5.02, 3.19, 3.05, 2.67, 2.37 | 4.0, 3.07 | 3.46, 3.41 | | | calc: 57.97, 6.11, 9.01, 10.30<br>found: 58.07, 6.06, 8.85, 10.23 |
| 47 | 7.50, 7.31 7.19 | 5.04, 3.21, 3.07, 2.70, 2.38 | 4.20, 3.09 | 3.95, 3.87 3.45, 3.38 1.35, 1.32 | | | calc: 59.16, 6.47, 8.62, 9.86<br>found: 59.23, 6.39, 8.52, 9.76 |

TABLE 10

Analytical Data of Compounds of the Invention shown in Table 6

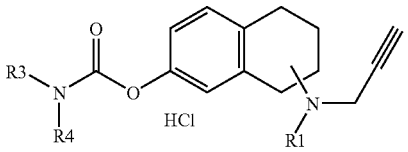

| # | NMR[4] aryl | cyclohex. | R1 | proparg. | R3, R4 | IR | MS ($MH^+$) | elem. anal. (C, H, N) |
|---|---|---|---|---|---|---|---|---|
| 40 | | | | | | | | calc:<br>found: |
| 41 | 7.22, 6.95 | 3.79, 3.26 2.95, 2.32 1.91 | | 4.06, 3.01 | 3.50, 3.36 3.09, 2.96 1.24, 1.16 | 3227, 2938 2768, 1718 1587, 1494 1394, 1301 | 287 | calc: 63.25, 7.18, 8.68<br>found: 63.16, 6.93, 8.69 |
| 42 | 7.21, 7.03 | 4.60, 2.81 2.72, 2.15 2.02, 1.84 1.80 | | 3.88, 3.95 | 3.01, 2.87 | 3234, 2936 2774, 2130 1732, 1499 1390 | 273 | calc: 62.23, 6.80, 9.07<br>found: 62.20, 7.01, 9.3 |
| 43 | 7.32, 7.12 | 4.65, 2.88 2.80, 2.20 2.12, 1.94 1.85 | | 3.99, 3.04 | 3.51, 3.37 3.10, 2.96 1.23, 1.16 | 3216, 2933 2768, 2663 2129, 1723 1425, 1399 | 287 | calc: 63.06, 7.41, 8.65<br>found: 63.2, 7.14, 8.81 |

[4]$D_2O$, unless specified otherwise

BIOLOGICAL EXAMPLES

Example 1

Acetylcholinesterase Inhibition in Mice 1.1 In vitro measurement of Acetylcholinesterase (AChE) Inhibition Human erythrocyte acetylcholinesterase (type XIII, Sigma Israel), was prepared in a stock solution of 1 U/ml, containing Triton (1%) and bovine serum albumin (0.05%) in phosphate buffer (pH 8). The enzyme (0.05U) was incubated with 3–5 different concentrations of test compound (in triplicate) for periods of from 15 to 60 minutes at 37° C. The substrate acetylthiocholine (0.075M) and 5,5'-dithiobis-(2-nitrobenzoic acid) (DTNB, 0.01M) were then added and the rate of hydrolysis of the substrate which yields a yellow product monitored spectrophotomerically at 412 nM (Ellman et al., Biochem Pharmacol. (1961) 7: 88–95). The percentage inhibition of AChE by each concentration of drug is calculated by comparison with that of enzyme in the absence of drug. The concentration of each drug that inhibits AChE by 50% ($IC_{50}$) at the time of peak activity was calculated and is given in Table 11 below.

1.2 Ex vivo measurement of Acetylcholinesterase (AChE) Inhibition

Test drugs or saline were administered sub-cutaneously to male mice (Sabra strain, 28–35 g). At least 4–5 mice were used per dose and a minimum of 3 doses per drug were tested. The mice were sacrificed 15, 30, 50, 70, 90, 120 or 180 minutes after drug administration, the brains rapidly removed (minus cerebellum), weighed and homogenized in 0.1 M phosphate buffer, pH 8.0, containing Triton (1 mg/100 g tissue) and centrifuged to remove cell debris. Aliquots (25 μl) of the supernatant were then incubated with acetylthiocholine and DTNB. AChE activity was measured as described above. The % inhibition of whole brain AChE by each dose of drug was calculated by comparison with enzyme activity from 3 saline treated control mice run at the same time. The dose of each drug that inhibits AChE by 50% at the peak of activity ($ED_{50}$) was calculated and is given in Table 11.

1.3 Acute Toxicity in Mice

Drugs were administered sub-cutaneously in at least 3 doses, to a minimum of 10 mice per dose. The dose that was lethal to 50% of the mice ($LD_{50}$) within 6 hours after administration was calculated for each drug and is given in Table 11. Therapeutic Ratio was calculated as $LD_{50}$ divided by ED50 of ex vivo acetylcholine esterase inhibition.

Example 2

2.1 Inhibition of MAC activity in vitro

The MAO enzyme source was a homogenate of rat brain in 0.3M sucrose, which was centrifuged at 600 g for 15 minutes. The supernatant was diluted appropriately in 0.05M phosphate buffer, and pre-incubated with serial dilutions of test compounds for 20 minutes at 37° C. $^{14}C$-Labeled substrates (2-phenylethylamine, hereinafter PEA; 5-hydroxytryptamine, hereinafter 5-HT) were then added, and the incubation continued for a further 20 minutes (PEA), or 30–45 minutes (5-HT). Substrate concentrations used were 50 μM (PEA) and 1 mM (5-HT). In the case of PEA, enzyme concentration was chosen so that not more than 10% of the substrate was metabolized during the course of the reaction. Deaminated products were extracted into toluene-ethyl acetate (1:1 v/v) containing 0.6% (w/v) 2,5-diphenyloxazole (ppo) prior to determination by liquid scintillation counting. Radioactivity n the eluate indicates the production of neutral and acidic metabolites formed as a result of MAO activity. Activity of MAO in the sample was expressed as a percentage of control activity in the absence of inhibitors after subtraction of appropriate blank values. The activity determined using PEA as substrate is referred to as MAO-B, and that determined using 5-HT as MAO-A.

Concentrations of inhibitor producing 50% inhibition of substrate metabolism ($IC_{50}$) were calculated from the inhibition curves, and are shown in Table 11.

2.2 Inhibition of MAO activity ex vivo

Male Sabra mice, weighing 45–50 g were injected with test compound solutions (prepared in 0.9% saline). Each dose was administered to two or three mice. The mice were sacrificed two hours after drug administration or at a time corresponding to the peak AChE inhibition time (see Table 11). The brain and liver were rapidly dissected and stored in appropriate vials on ice. The tissues were weighed, diluted to ½ in sucrose 0.3M and stored at −20° C. before performance of the MAO assay described above. The results given in Table 11 relate to measurements made on brain tissue only.

2.3 Inhibition of MAO activity following sub-acute administration to rats

Experiments were done in Sprague Dawley male rats. Procedures were repeated as described in Examples 2.1 and 2.2 but drug administration was continued daily for 14 days. At the end of this period animals were sacrificed and MAO levels determined in the brain, liver and intestines. Compounds 24, 25, 37 and 39 were administered subcutaneously and/or pet os at a dose of 6 mg/kg(sc) and 10 mg/kg(po) (compound 24), 25 and 50 mg/kg (compound 25), 45 mg/kg (compound 37) and 40 mg/kg (compound 39). The results are shown in Table 11a from which it can be seen that these compounds displayed selectivity in inhibiting MAO enzyme sub-types in the brain in preference to the periphery.

TABLE 11

| | AChE Inhibition | | Time | | MAO-B Inhibition | | MAO-A Inhibition | | Acute Toxicity | |
|---|---|---|---|---|---|---|---|---|---|---|
| | | Ex vivo | | to return to | | | | | | |
| # | In vitro IC50 μm | ED50 μmoles/kg (AC) | to peak activity t (min) | 50% of peak t (min) | In vitro IC50 μm | Ex vivo ED50 μmoles/kg | In vitro IC50 μm | Ex vivo ED50 μmoles/kg | LD50 μmoles/kg (LD) | Therapeutic Ratio LD/AC |
| 1 | 0.6 | 5.0 | 30 | >120 | >1000 | >>80 | 75 | >>80 | 83.8 | 16.8 |
| 23 | 3.5 | 22.4 | 15 | 70 | 600 | 100 | 800 | >120 | 255 | 11.4 |
| 2 | 7.3 | NT | | | >1000 | | 32 | | | |
| 3 | 20.0 | 46.3 | 60–90 | >180 | >1000 | | 12.6 | | 950 | 20.6 |
| 25 | 53.0 | 140.0 | 60 | >180 | >1000 | 200 | 270 | >>350 | 1400 | 10.8 |
| 26 | 17.0 | 120 | 30–60 | | 264 | 333 | 114 | >>440 | 1200 | 9 |
| 27 | 5.72 | 30 | 15 | >60 | >1000 | >>160 | >1000 | >>160 | 300 | 10 |
| 28 | 100.0 | NT | | | | | | | | |
| 5 | 11.5 | 85.0 | 60 | >120 | | >>277 | | >>277 | 840 | 9.9 |
| 7 | 32.0 | NT | | | >1000 | | 600 | | | |
| 8 | 1.0 | 10.0 | 15–30 | >60 | >1000 | >>50 | 50 | >>50 | 87 | 8.7 |
| 9 | 0.18 | 19 | 15 | | | | | | 93 | 4.9 |
| 29 | 8.5 | 53.7 | 15 | >60 | 40 | 30 | 40 | 50 | 500 | 9.3 |
| 10 | 38.0 | 34.7 | 60–90 | >180 | >1000 | >175 | 22 | >175 | 740 | 21.3 |
| 30 | 1300.0 | NT | | | | | | | | |
| 31 | 10.0 | 110 | | | >1000 | >100 | >1000 | >100 | | |
| 32 | 3.7 | 7.8 | 15 | | 500 | >>20 | 190 | >>20 | 68 | 9.0 |
| 12 | 2.0 | 8.0 | 15 | | >1000 | | 130 | | <20 | <2.5 |
| 33 | 540.0 | NT | | | >1000 | 1000 | >1000 | >>1200 | | |
| 34 | 0.046 | 0.65 | 30 | | 100 | | 0.5 | | 3.7 | 5.7 |
| 35 | 2.2 | 10 | 60 | | 100 | | <1 | | 33 | 3.3 |
| 37 | 51 | 125 | | | 500 | 200 | 750 | >200 | 1700 | 13.6 |
| 39 | 36 | 80 | 30–60 | >180 | 1000 | >>200 | 550 | >>200 | 1150 | 14.4 |
| 24 | 3 | 16.6 | 15 | | 750 | 100 | 850 | >120 | 179 | 10.8 |
| 60 | 42 | | | | | | | | | |
| 58 | 51 | | | | >1000 | | 300 | | | |
| 54 | 1.8 | | | | | >100 | | >100 | | |
| 55 | 2 | | | | | >100 | | >100 | | |

TABLE 11-continued

| | AChE Inhibition | | Time | | MAO-B Inhibition | | MAO-A Inhibition | | Acute Toxicity | |
|---|---|---|---|---|---|---|---|---|---|---|
| # | In vitro IC50 μm | Ex vivo ED50 μmoles/kg (AC) | to peak activity t (min) | to return to 50% of peak t (min) | In vitro IC50 μm | Ex vivo ED50 μmoles/kg | In vitro IC50 μm | Ex vivo ED50 μmoles/kg | LD50 μmoles/kg (LD) | Therapeutic Ratio LD/AC |
| 56 | 11.5 | 180 | | | | | | | | |
| 57 | 2.4 | 70 | | | 25 | | 89 | | | |
| 48 | 10 | | | | | | | | | |
| 49 | 2 | | | | | | | | | |
| 17 | 4 | | | | | | | | | |
| 16 | 9 | | | | | | | | | |
| 50 | 0.26 | | | | | | | | | |
| 61 | 0.75 | 47 | | | 500 | >100 | 700 | >100 | | |
| 64 | 1.9 | 13.2 | | | >1000 | >120 | 1000 | >120 | 150 | 11.4 |
| 38 | 33 | >1000 | | | 10 | >400 | 170 | >400 | | |
| 36 | 15 | >400 | | | >1000 | >100 | >1000 | >100 | >1000 | |
| 62 | 0.57 | 290 | 60 | | 100 | >>200 | 80 | >>200 | | |
| 63 | 2.5 | 140 | 60–90 | | 120 | >300 | 40 | >300 | 1300 | 9.3 |
| 71 | 29 | >100 | | | | 130 | | >100 | | |
| 72 | 38 | >200 | | | | >100 | | >100 | | |
| 78 | 10 | 101 | 60–90 | >120 | | 450 | | >>450 | 1300 | 12.9 |
| 79 | 9.4 | 94 | 90 | >180 | | >>450 | | >>450 | 1000 | 10.6 |
| 81 | 11.5 | 40 | 90 | >120 | | >>100 | | >>100 | 920 | 23 |
| 83 | 80 | | | | | | | | | |
| 86 | 10.5 | | | | | | | | | |
| 87 | 9.1 | | | | | | | | | |
| 85 | 17 | >100 | | | | | | | | |

TABLE 11a

Effect of Compounds 24, 25, 37 and 39 on MAO activity after chronic sub-acutetreatment to rats

| | | % MAO-A inhibition | | | | | % MAO-B inhibition | | | | |
|---|---|---|---|---|---|---|---|---|---|---|---|
| Compound | | 24 | 25 | | 37 | 39 | 24 | 25 | | 37 | 39 |
| Dose (mg/kg) | | 6 (sc) 10 (po) | 25 | 50 | 45 | 40 | 25 | 25 | 50 | 45 | 40 |
| Brain | sc | 30 | 53 | 75 | 78 | 17 | 50 | 61 | 85 | 87 | 27 |
| | po | 0 | | 70 | 67 | | 20 | | 80 | 82 | |
| Intestine | sc | 0 | 0 | 30 | 0 | 0 | 0 | 29 | 45 | 26 | 40 |
| | po | 30 | | 25 | 0 | | 20 | | 30 | 21 | |
| Liver | sc | 0 | 0 | 10 | 0 | 0 | 0 | 14 | 40 | 29 | 0 |
| | po | 10 | | 25 | 28 | | 0 | | 35 | 28 | |

Example 3

Effect of Drug Treatment Following Closed Head Injury (CHI) in Mice

The procedure for closed head injury followed was as described for rats in Shohami, et al. (J Neurotrauma (1993) 10 (2): 109–119) with changes as described.

Animals: Male Sabra mice (Hebrew University strain) weighing 34–40 g were used. They were housed in groups of 10 per cage, in a 12 hr:12 hr light:dark cycle. Food and water were provided ad libitium.

Trauma was induced under ether anesthesia. A longitudinal incision was performed in the skin covering the skull and the skin retracted to expose the skull. The head was fixed manually at the lower plane of the impact apparatus. A weight of 333 g was delivered by an electric device from a distance of 3 cm to the left hemisphere, 1–2 mm lateral to the midline in the midcoronal plane. Test compounds were injected sub-cutaneously at a dosage corresponding to the $ED_{50}$ acetylcholinesterase, once 15 min. after CHI.

3.1 Assessment of Motor Function

Motor function and reflexes were evaluated in the injured mice at different times after closed head injury (CHI) using a neurological severity score (NSS) as shown in Table 12 below, which is modified from that described for rats (Shohami, et al. supra.). One point was awarded for the lack of a tested reflex or for the inability to perform the tasks outline in the Table. The maximal score that can be reached at 1 hour post-CHI is 25 points and 21 at later times. The difference in NSS at 1 hr and at any other time reflects the recovery, and is referred to as ΔNSS. An NSS score of 15–19 at 1 hr denotes severe injury, 11–14 moderate injury and less than 10 mild injury. The NSS recorded after treatment with test compound or control is shown in Table 13.

TABLE 12

Neurological Severity Score for mice after Closed Head Injury

| Parameter | Points at 1 hour | Points at any other time |
|---|---|---|
| Inability to exit from a circle (30 cm diameter when left in its center | | |
| for 30 min | 1 | |
| for 60 min | 1 | |
| for >60 min | 1 | 1 |
| Loss of righting reflex | | |
| for 10 second | 1 | |
| for 20 seconds | 1 | |
| for >30 seconds | 1 | 1 |
| Hemiplegia - inability of mouse to resist forced changes in position | 1 | 1 |
| Flexion of hind limb when lifted by tail | 1 | 1 |
| Inability to walk straight when placed on the floor | 1 | 1 |

TABLE 12-continued

| Neurological Severity Score for mice after Closed Head Injury | | |
|---|---|---|
| Parameter | Points at 1 hour | Points at any other time |
| Reflexes | | |
| Pinna reflex | 1 | 1 |
| Corneal reflex | 1 | 1 |
| Startle reflex | 1 | 1 |
| Clinical grade | | |
| Loss of seeking behaviour | 1 | 1 |
| Prostration | 1 | 1 |
| Loss of reflexes | | |
| Left forelimb | 1 | 1 |
| Right forelimb | 1 | |
| Left hindlimb | 1 | 1 |
| Right hindlimb | 1 | 1 |
| Functional test | | |
| Failure in beam balancing task (0.5 cm wide) | 1 | 1 |
| for 20 seconds | 1 | 1 |
| for 40 seconds | 1 | 1 |
| for >60 seconds | | |
| Failure in round stick balancing task (0.5 cm is diameter | | |
| for 10 seconds | 1 | 1 |
| Failure in beam walking task | | |
| 3 cm wide | 1 | 1 |
| 2 cm wide | 1 | 1 |
| 1 cm wide | 1 | 1 |
| Maximum Points | 25 | 21 |

TABLE 13

| Change in Neurological Severity Score after Closed Head Injury in Mice | | | | |
|---|---|---|---|---|
| Drug/dose | N | ΔNSS, 24 hr post-CHI | ΔNSS, 7 days post-CHI | ΔNSS, 14 days post-CHI |
| Saline, 1 ml/kg | 51 | 4.75 ± 0.17 | 5.83 ± 0.36 | 5.96 ± 0.4 |
| 1 (1.3 mg/kg) | 10 | 5.50 ± 0.34[m] | 7.31 ± 0.45[m] | 9.21 ± 0.47 |
| 24 (6.5 mg/kg) | 12 | 6.31 ± 0.23[m] | 8.67 ± 0.41[m] | 9.67 ± 0.66[m] |
| 25 (46 mg/kg) | 10 | 5.00 ± 0.42 | 7.42 ± 0.62[m] | 9.01 ± 0.69[m] |
| 25[1] (46 mg/kg) | 10 | 4.90 ± 0.43 | 7.70 ± 0.33[m] | 8.80 ± 0.33[m] |
| 10 (15 mg/kg) | 11 | 5.36 ± 0.39 | 6.64 ± 0.41[m] | 6.73 ± 0.52 |
| 37 (30 mg/kg) | 12 | 5.50 ± 0.26 | 6.92 ± 0.38 | 8.25 ± 0.62 |
| 39 (30 mg/kg) | 14 | 5.36 ± 0.25 | 6.71 ± 0.45 | 7.64 ± 0.48 |

[1]administered 60 min before CHI
[m]significantly different from saline control ($p < 0.05$)

3.2 Assessment of Reference Memory

Morris Water Maze Test: the water maze consists of a circular aluminium pool, im in diameter and 60 cm in depth, filled with water to a depth of 17.5 cm. The hidden goal platform is a glass vessel (15 cm diameter×16.5 cm height) placed upside down at a fixed location in the pool, 1 cm below the surface of the water. The water temperature is maintained at 24° C. and the pool is always placed in the same position in the room to provide the same extra-maze cues. Prior to CHI (as described in Example 3 above), mice were given 3 trials per day for 5 consecutive days to establish a baseline performance—measured as the latency to find the platform from the same start location. Commencing 24 hr after CHI, mice were retested daily for 2 weeks in 3 trials per day.

Figure 2:
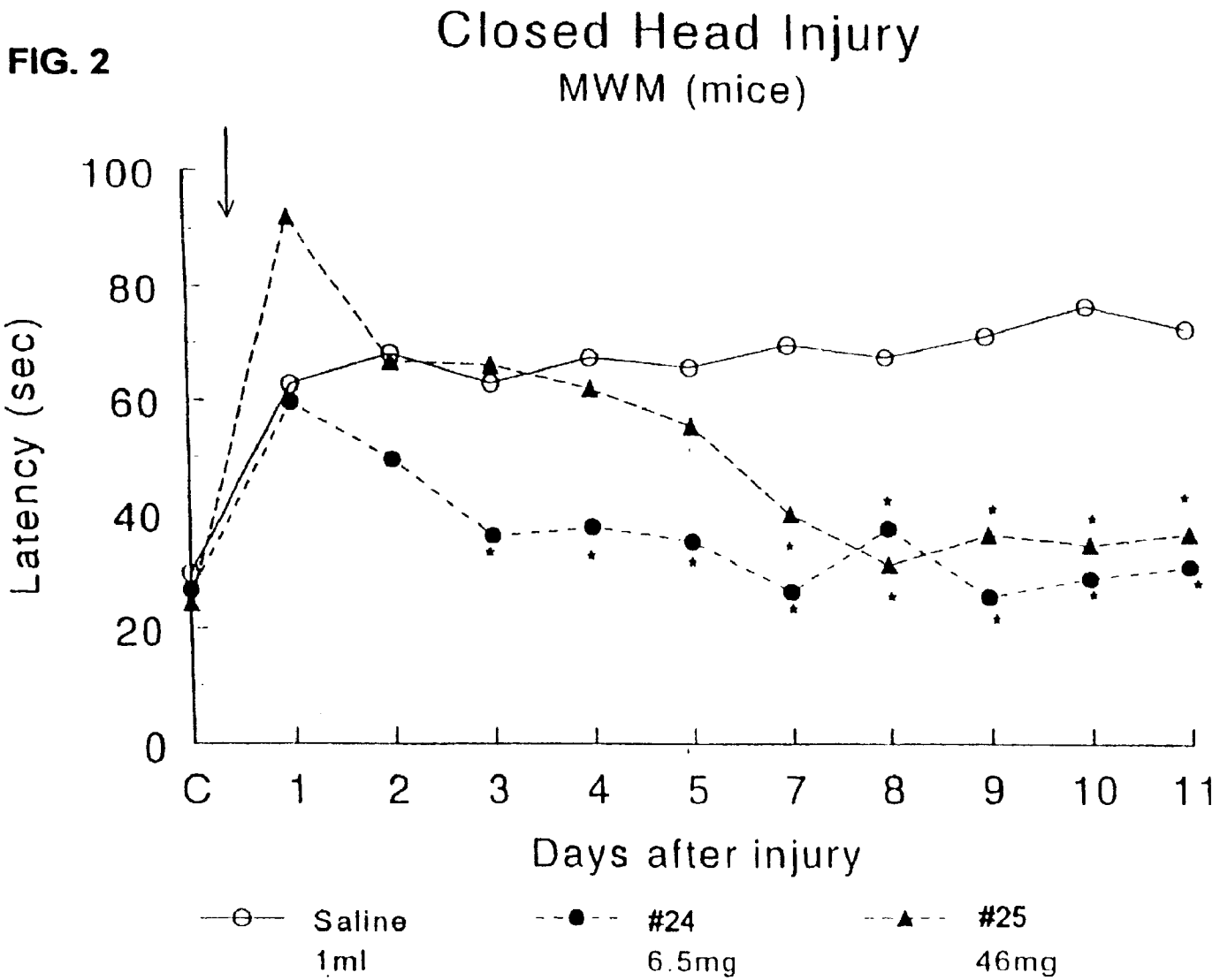
FIG. 2 shows the reduction in latency for mice after closed head injury in the Morris Water Maze Test after treatment with compound 24, compound 25 or Saline (Control) The arrow shows the time of closed head injury.
Figure 3:
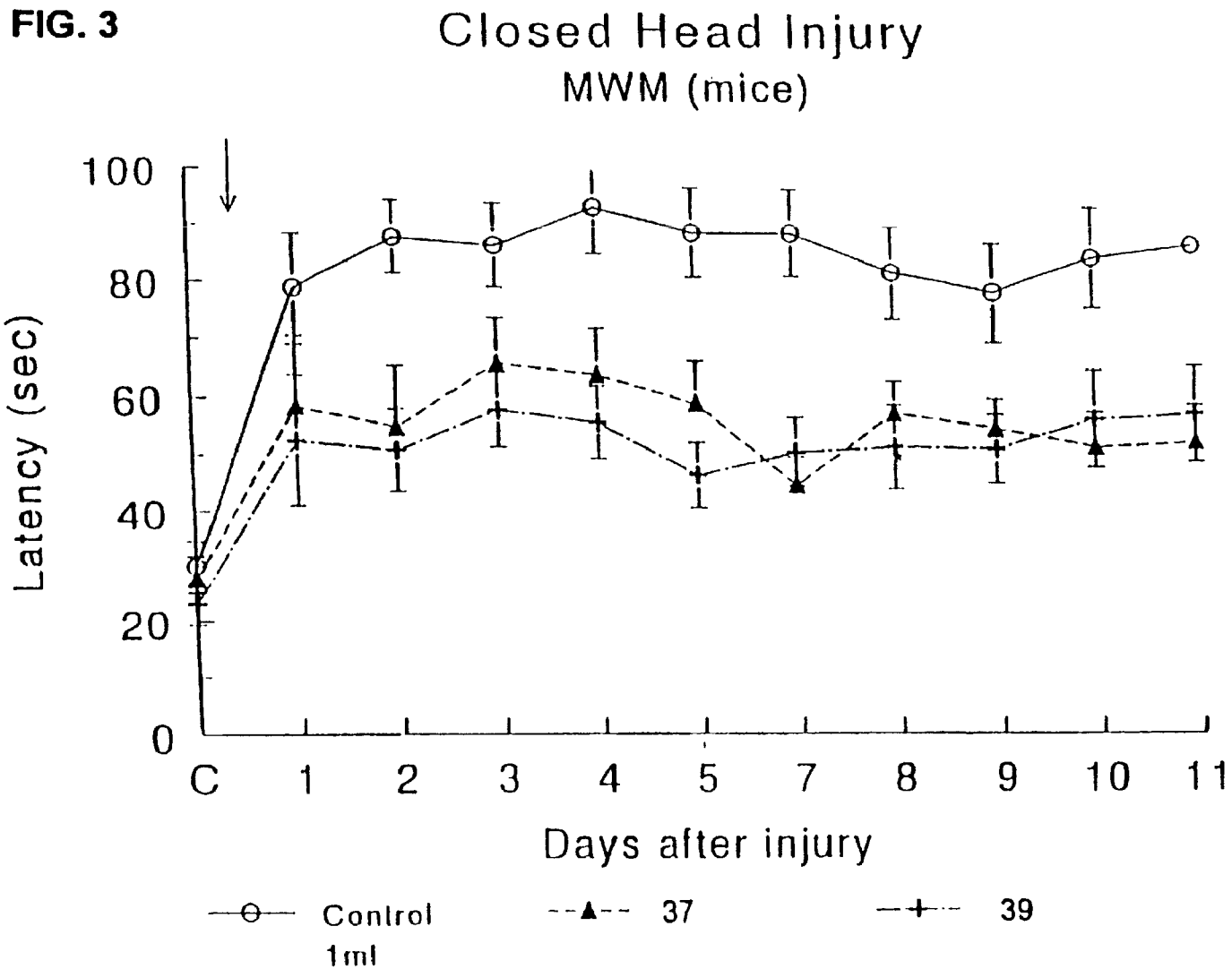
FIG. 3 shows the reduction in latency for mice after closed head injury in the Morris Water Maze Test after treatment with compound 37, compound 39 or Saline (Control). The arrow shows the time off closed head injury.

FIGS. 1, 2 and 3 show the reduction in latency for mice treated with compounds 24 (6.5 mg/kg), 25 (46 mg/kg), 1 (1.3 mg/kg), 10 (15 mg/kg), 37 (30 mg/kg) or 39 (30 mg/kg) compared to saline treated controls after CHI. It appears that immediately post-CHI mice forget the location of the goal. Memory is enhanced following treatment with test compounds, as compared to saline treated mice. In the Figures the arrow shows the time of CHI.

Example 4

Effect On Mice Having Experienced A Hypobaric Hypoxic Episode

The hypobaric hypoxic model is a well accepted model for assessing the activity of compounds believed to possess neuroprotective activity. The model is based on that described in Nakanishi, M., et al. Life Sci. (1973) 13: 467, Oshiro, et al., J. Med. Chem. (1991) 34: 2004–2013 and U.S. Pat. No. 4,788,130.

A 12 liter desiccator (desiccator A) and a 2.5 liter desiccator (desiccator B) were separately connected to a vacuum pump. Desiccator B was disconnected and allowed to equilibrate with room air whilst desiccator A was evacuated to a pressure of 100 mmHg. Four male ICR albino mice (22–28 g) were placed in desiccator B. Desiccator B was then closed to room air and connected to desiccator A. The pressure inside desiccator B was monitored using a mercury manometer and at the point were the pressure in desiccator B reached 200 mmpg (usually within 14 seconds), the two desiccators were disconnected from the vacuum pump and the pump switched off. The survival time from the moment of induction of hypoxia to the time of cessation of respiration was recorded for each mouse for a maximum of 15 minutes after which time room air was reintroduced to desiccator B. Survivors were monitored for signs of lethargy or vitality.

Effect of drug treatment was assessed as the percent of the survival time of the drug treated group with respect to the saline injected or vehicle injected control group. Control groups were run twice, before and after each experimental group and consisted of 8 mice in groups of 4 mice to ensure a constant residual volume of oxygen in all tests. The effect of each dose of test drug was determined in duplicate i.e. two groups of 4 mice. The range of survival times of control mice was from 108–180 seconds.

Positive reference drugs were sodium pentobarbital at a dose of 40 mg/kg, and diazepam 10 mg/kg given 0.5 h prior to hypoxia, physostigmine 0.2 and 0.4 mg/kg and neostigmine 0.2 mg/kg given sc 30 min before hypoxia. Methyl atropine 1 mg/kg was given sc. 10 min. before physostigmine.

Test drugs were dissolved in 0.9% saline, and injected sc. in the nip of the neck at a dose in accordance with body weight, 60–90 min. before hypoxia. The volume of injection was 0.2–0.3 mL per mouse (10 mL/kg). The initial dose was about one third of the reported $LD_{50}$ for acetylcholine esterase inhibition. If no protection could be obtained, the dose was further increased to the nearest non-toxic dose. In case of protection, the dose was further reduced in an attempt to locate the "protective" dose range.

Per cent survival times as compared to saline treated control is shown in Table 14.

TABLE 14

Survival Time of Mice Having Experienced a Hypobaric Episode

| Compound | Dose mg/kg | Time of dose (min before hypoxin) | Protection (% of control) | p |
|---|---|---|---|---|
| Control (saline) | | | 100 | |
| Nembutal | 40 | 30 | 253 ± 200 | <0.005 |
| Diazepam | 10 | 30 | 316 ± 78 | <0.003 |
| Neostigmine | 0.2 | 30 | 141 ± 32 | <0.01 |
| Physostigmine | 0.2 | 30 | 453 ± 222 | <0.001 |
| | 0.4 | 30 | 552 ± 210 | <0.001 |
| Physostigmine | 0.4 | 30 | 296 ± 193 | <0.05 |
| and Atropine | 1.0 | 40 | | |
| methyl nitrate | | | | |
| 1 | 8 | 60 | 637 ± 116 | 0.007 |
| | 4 | 60 | 470 ± 200 | 0.001 |
| | 2 | 60 | 120 ± 51 | NS |
| 24 | 50 | 60 | 738 ± 00 | <0.001 |
| | 21 | 60 | 269 ± 166 | <0.02 |
| 25 | 100 | 60 | 761 ± 91 | 0.001 |
| | 75 | 60 | 559 ± 225 | 0.001 |
| | 50 | 60 | 380 ± 231 | 0.01 |
| | 25 | 60 | 84 ± 35 | NS |
| 27 | 50 | 60 | 455 ± 23 | <0.001 |
| | 3 | 60 | 287 ± 319 | <0.001 |
| | 15 | 60 | 143 ± 56 | <0.05 |
| | 8 | 60 | 119 ± 45 | NS |
| 29 | 77 | 60 | 508 ± 206 | <0.001 |
| | 53 | 60 | 638 ± 10 | <0.001 |
| | 25 | 60 | 131 ± 56 | NS |
| | 25 | 30 | 273 ± 183 | <0.02 |
| 10 | 50 | 90 | 705 ± 101 | 0.001 |
| | 25 | 90 | 700 ± 201 | 0.001 |
| | 10 | 90 | 304 ± 129 | 0.001 |
| 12 | 20 | 60 | 725 ± 128 | <0.001 |
| | 15 | 60 | 649 ± 221 | <0.001 |
| | 10 | 60 | 386 ± 238 | <0.01 |
| | 7 | 60 | 248 ± 97 | <0.001 |

Example 5

Neurological Score and Brain Infarct Size in Male Wistar Rats After Middle Cerebral Artery Occlusion (MCA-O)

A modification of the procedure described by Tamura, et al was used (Tamura A, Graham D1, McCulloch J, Teasdale G H (1981) J. Cereb. Blood Flow and Metab. 1: 53–60). Male Wistar rats (Olac England-Jerusalem) 300–400 g each were anesthetized with a solution of Equitesine administered i.p. at a dose of 3 ml/kg. Equitesine consists of 13.5 ml sodium pentothal solution (60 mg/ml), 3.5 g chloral hydrate, 1.75 g $MgSO_4$, 33 ml propylene glycol, 8.3 ml absolute alcohol, made up to 83 ml with distilled water.

Surgery was performed with the use of a high magnification operating microscope, model SMZ-2B, type 102 (Nikon, Japan) In order to expose the left middle cerebral artery, a cut was made in the temporal muscle. The tip of the coronoid process of mandible was excised as well and removed with a fine rongeur. Craniectomy was made with a dental drill at the junction between the median wall and the roof of the inferotemporal fossa.

The dura matter was opened carefully using a 27 gauge needle The MCA was permanently occluded by microbipolar coagulation at low power setting, beginning 2–3 mm medial to the olfactory tract between its cortical branch to the rhinal cortex and the laterate striate arteries. After coagulation, the MCA was severed with microscissors and divided to ensure complete occlusion. Following this, the temporalis muscle was sutured and laid over the craniectomy site. The skin was closed with a running 3-0 silk suture. A sham craniectomy operation was performed on a parallel group of rats, but without cauterization of the MCA.

During the entire surgical operation (20–25 min) in either group, body temperature was maintained at 37 to 38° C. by means of a body-temperature regulator (Kyoristsu, Japan) consisting of a self-regulating heating pad connected to a rectal thermistor. At 24 and 48 hours post surgery a neurological score was taken in order to assess the severity of the injury in the drug-treated rats with respect to their untreated controls.

Drugs were administered as an s.c. injection, according to the following schedule:

Compound 24: 7.8 mg/kg 15 minutes prior to MCA-O and 6.5 mg/kg 2 hours post MCA-O.

Compound 25: 43 mg/kg 90 minutes prior to MCA-O and 30 mg/kg 3 hours post MCA-O.

After 48 hours of ischemia induced by permanent occlusion morphometric, the animals-were anesthetized with Equitesine and measurement of infarct volume was performed as follows by TTC (2,3,5-triphenyl tetrazolium chloride) staining. TTC 1% in saline was prepared immediately before use and protected from exposure to light by aluminum foil wrap. MCA-O rats were deeply anesthetized and a 23-gauge butterfly needle with an extended tubing and a 20 ml syringe was inserted into the ventricle via thoracotomy. The right atrium was incised to allow outflow of saline. Heparine 50 i.u. in saline was delivered until the perfusate was bloodless. A 30-ml TTC-filled syringe was exchanged for the saline syringe and TTC was injected into the left ventricle at a rate of 5 ml/min. Both perfusate solutions were administered at 37.5° C. The brains were removed and immersed into 20 ml of 1% TTC contained in tightly closed glass vials. These were further placed for 2 hours in a water bath maintained at 37° C. The TTC solution was decanted, the brains removed, wiped dry and placed into 10% buffered formalin solution for 3 days. Six coronal slices each 2 mm thick, 3, 5, 7, 9, 11 and 13 mm distal from the frontal pole were obtained with a brain matrix (Harvard Apparatus, South Natick, Mass.). Infarction areas were measured with a video imaging and analyzer from both sides of the coronal slices and expressed in $mm^2$. The volume of the infarcted region in mm was calculated by taking the sum of the ischemic areas in all six slices. The volume of infarcted region for the saline control and compounds 24 or 25 are given in Table 15a.

Neurological Score

The neurological score was measured in a manner slightly different from that given in Example 3. This method consists of the sum total of a series of ratings assigned to the performance of specific locomotor activities in a given rat. The scale runs from 0 (fully normal rats) to 13 (fully incapacitated rats). Most parameters are rated as either 0 (normal), or 1 (incapacitated) others are graded. The following tests were used in the present study:

General observation tests: hypoactivity, sedation, piloerection.

Motor reflex. Rats were lifted by the tail about 15 cm above the floor. Normal rats assume a posture in which they extend both forelimbs towards the floor and spread that hind limbs to the sides in a trapeze-like manner. MCAO, when severe, causes consistent flexion of the contralateral limb.

Motor ability. This is seen as the ability to grasp a rod 1 cm in diameter by the contralateral limb for 5–15 sec when the rat is left hanging on the rod through the arm pit.

Motor coordination. Normal rats are able to walk up and down a beam, 5 cm wide placed at a moderate slant. Failure to walk the beam in either direction reveals some motor incoordination, lack of balance and limb weakness.

Gait. Ability to restore normal position to either hand contralateral or fore contralateral limb when intentionally displaced while on a narrow beam.

Balance. Ability to grasp and balance on a narrow beam 2 cm wide.

Locomotor activity. Total movements over a period of 15 min in an automated activity cage.

Ratings assigned to each of the above parameters are given in Table 15.

TABLE 15

Neurological scores assigned to each of 10 parameters of posture and locomotion

| | Parameter | Score | |
|---|---|---|---|
| a. | Activity in home cage | normal = 0 | hypoactive = 1 |
| b. | Sedation | none = 0 | marked = 1 |
| c. | Piloerection | none = 0 | marked = 1 |
| d. | Extenstion of contralateral forelimb towards floor when lifted by tail | good = 0 | flexed limb = 1 |
| e. | Spread of contralateral hind limb when lifted by tails (trapezoid posture) | good = 0 | flexed limb = 1 |
| f. | Grasp rod with contralateral limb for 5–15 sec. when suspended by armpit | good = 0 | poor = 1 |
| g. | Walk on beam 5 cm wide | good = 0 | poor = 1 |
| h. | Restoration of contralateral hind and/or forelimb to original position when intentionally displaced | good = 0 | poor = 1 (one limb) 2 (two limbs) |
| i. | Grasping & balance on beam 2 cm wide | good = 0 | poor = 1 |
| j. | Motor activity with respect to control (15 min in activity cage) | 0–25% of control = 3<br>26–50% of control = 2<br>51–75% of control = 1<br>76–100% of control = 0 | |
| k. | Tendency to lean on contralateral side | 1 | |
| l. | Contralateral circling when pulled by tail | 1 | |
| m. | Contralateral circling spontaneous. | 1 | |

Table 15a shows the effect of compounds 24 and 25 in this model, comparing the change in NSS measured in 24 and 48 hours post injury.

TABLE 15a

| Compound | ΔNSS* | Volume infarction Mean ± SD mm* |
|---|---|---|
| Saline | 0.745 | 211 ± 75 |
| 24 | 1.625 | 152 ± 45 |
| 25 | 1.78 | 189 ± 54 |

*Difference is ΔNSS measured at 24 hours and 48 hours. From this it can be seen that compounds 24 and 25 have a longer lasting effect than the saline treated control.

SCHEME I

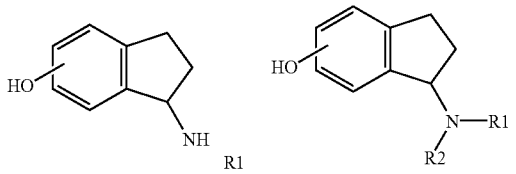

-continued

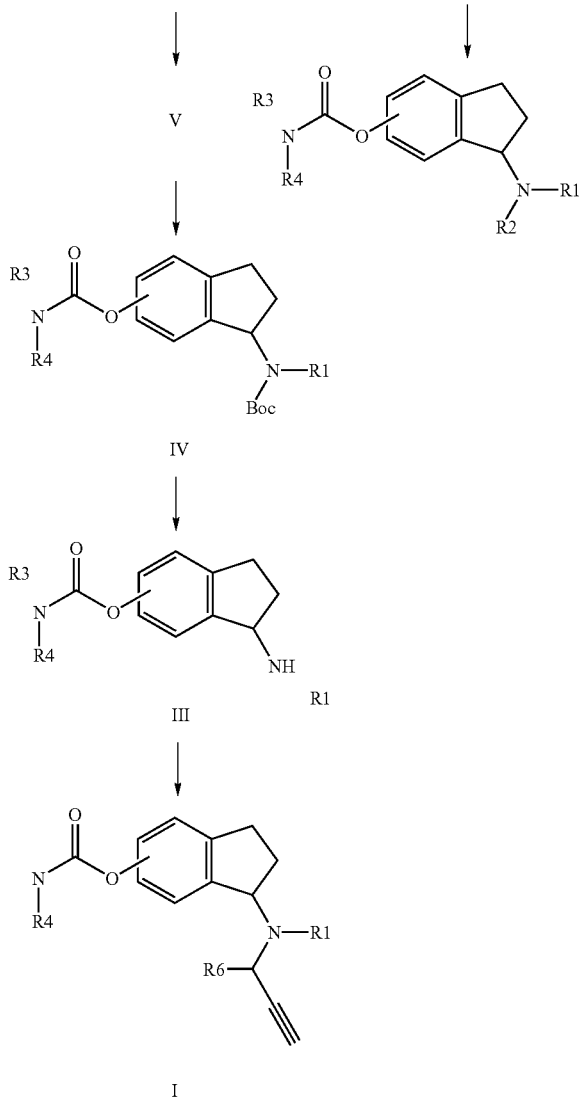

What is claimed is:

1. A method of treating a subject suffering from depression comprising administering to the subject a therapeutically effective amount of a compound having the structure:

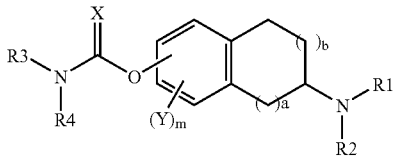

wherein when a is 0, b is 1 or 2, *and when a is 1, b is 1*; [wherein when a is 1, b is 1,] m is 0–3[,]; X is O or S[,]; Y is halogeno[,]; $R_1$ is hydrogen or $C_{1-4}$ alkyl[,]; $R_2$ is hydrogen, $C_{1-4}$ alkyl, *propargyl,* or [optionally] substituted propargyl; and $R_3$ and $R_4$ are each independently [hydrogen,] $C_{1-8}$ alkyl, $C_{6-12}$ aryl, $C_{6-12}$ [aryl] *aralkyl* or $C_{6-12}$ cycloalkyl, each *of which may be* optionally substituted, *or is hydrogen, such compound being a racemic mixture, an enantiomer, or a salt thereof;*

[a racemic mixture, an enantiomer, or salt thereof,] *so as* to thereby treat the subject's depression.

2. The method of claim 1 wherein the enantiomer is the R enantiomer.

3. The method of claim 1 wherein the enantiomer is the S enantiomer.

4. The method of claim 1 wherein the compound has the structure:

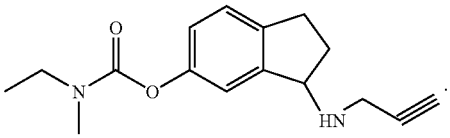

5. The method of claim 4 wherein the enantiomer is the R enantiomer.

6. The method of claim 4 wherein the enantiomer is the S enantiomer.

7. The method of claim 1 wherein the compound has the structure:

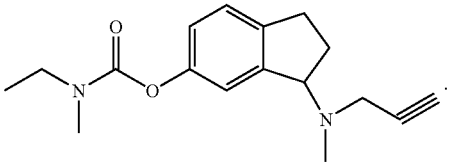

8. The method of claim 7 wherein the enantiomer is the R enantiomer.

9. The method of claim 7 wherein the enantiomer is the S enantiomer.

10. A method of selectively inhibiting monoamine oxidase-B (MAO-B) activity in the brain of a subject in need of such inhibition comprising administering to the subject a therapeutically effective amount of a compound having the structure:

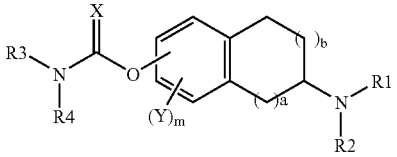

wherein when a is 0, b is 1 or 2, *and when a is 1, b is 1*; [wherein when a is 1, b is 1,] m is 0–3[,]; X is O or S[,]; Y is halogeno[,]; $R_1$ is hydrogen or $C_{1-4}$ alkyl[,]; $R_2$ is hydrogen, $C_{1-4}$ alkyl, *propargyl,* or [optionally] substituted propargyl; and $R_3$ and $R_4$ are each independently [hydrogen,] $C_{1-8}$ alkyl, $C_{6-12}$ aryl, $C_{6-12}$ [aryl] *aralkyl* or $C_{6-12}$ cycloalkyl, each *of which may be* optionally substituted, *or is hydrogen, such compound being a racemic mixture, an enantiomer, or a salt thereof;*

[a racemic mixture, an enantiomer, or salts thereof,] *so as* to thereby selectively inhibit MAO-B activity in the brain of the subject.

11. The method of claim 10 wherein the enantiomer is the R enantiomer.

12. The method of claim 10 wherein the enantiomer is the S enantiomer.

13. The method of claim 10 wherein the compound has the structure:

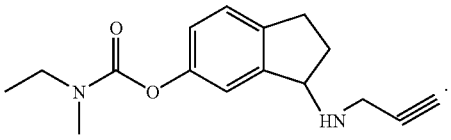

14. The method of claim 13 wherein the enantiomer is the R enantiomer.

15. The method of claim 13 wherein the enantiomer is the S enantiomer.

16. The method of claim 10 wherein the compound has the structure:

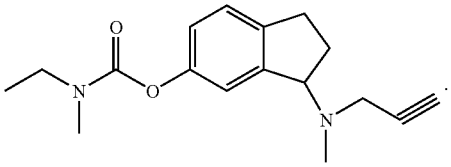

17. The method of claim 16 wherein the enantiomer is the R enantiomer.

18. The method of claim 16 wherein the enantiomer is the S enantiomer.

19. A method of treating a subject suffering from depression comprising administering to the subject a pharmaceutical composition comprising a therapeutically effective amount of a compound having the structure:

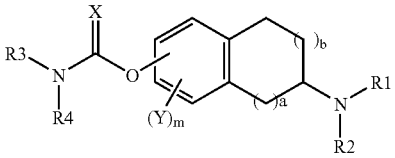

wherein when a is 0, b is 1 or 2, *and when a is 1, b is 1;* [wherein when a is 1, b is 1,] m is 0–3[,]; X is O or S[,]; Y is halogeno[,]; $R_1$ is hydrogen or $C_{1-4}$ alkyl[,]; $R_2$ is hydrogen, $C_{1-4}$ alkyl, *propargyl,* or [optionally] substituted propargyl; and $R_3$ and $R_4$ are each independently [hydrogen,] $C_{1-8}$ alkyl, $C_{6-12}$ aryl, $C_{6-12}$ [aryl] *aralkyl* or $C_{6-12}$ cycloalkyl, each *of which may be* optionally substituted, *or is hydrogen, such compound being a racemic mixture, an enantiomer, or a salt thereof* [a racemic mixture, an enantiomer, or salt thereof], and a pharmaceutically acceptable carrier[,]; *so as* to thereby treat the subject's depression.

20. The method of claim 19 wherein the pharmaceutically acceptable carrier is a solid and the therapeutically effective amount is an amount from about 0.5 mg to about 2000 mg.

21. The method of claim 19 wherein the pharmaceutically acceptable carrier is a liquid and the therapeutically effective amount is an amount from about 0.5 mg to about 2000 mg.

22. The method of claim 19 wherein the pharmaceutically acceptable carrier is a gel and the therapeutically effective amount is an amount from about 0.5 mg to about 2000 mg.

23. The method of claim 19 wherein the therapeutically effective amount is an amount from about 1 mg to about 1000 mg.

24. A method of selectively inhibiting monoamine oxidase-B (MAO-B) activity in the brain of a subject in need of such inhibition comprising administering to the subject a pharmaceutical composition comprising a therapeutically effective amount of a compound having the structure:

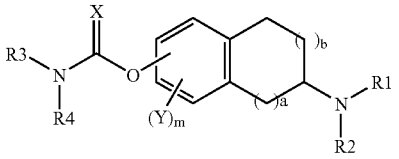

wherein when a is 0, b is 1 or 2, *and when a is 1, b is 1*; [wherein when a is 1, b is 1,] m is 0–3[,]; X is O or S[,]; Y is halogeno[,]; $R_1$ is hydrogen or $C_{1-4}$ alkyl[,]; $R_2$ is hydrogen, $C_{1-4}$ alkyl, *propargyl* or [optionally] substituted propargyl; and $R_3$ and $R_4$ are each independently [hydrogen,] $C_{1-8}$ alkyl, $C_{6-12}$ aryl, $C_{6-12}$ [aryl] *aralkyl* or $C_{6-12}$ cycloalkyl, each *of which may be* optionally substituted, *or is hydrogen, such compound being a racemic mixture, an enantiomer, or a salt thereof* [a racemic mixture, an enantiomer, or salt thereof], and a pharmaceutically acceptable carrier[,]; *so as* to thereby selectively inhibit MAO-B activity in the brain of the subject.

25. The method of claim 24 wherein the pharmaceutically acceptable carrier is a solid and the therapeutically effective amount is an amount from about 0.5 mg to about 2000 mg.

26. The method of claim 24 wherein the pharmaceutically acceptable carrier is a liquid and the therapeutically effective amount is an amount from about 0.5 mg to about 2000 mg.

27. The method of claim 24 wherein the pharmaceutically acceptable carrier is a gel and the therapeutically effective amount is an amount from about 0.5 mg to about 2000 mg.

28. The method of claim 24 wherein the therapeutically effective amount is an amount from about 1 mg to about 1000 mg.

*29. A compound having the structure:*

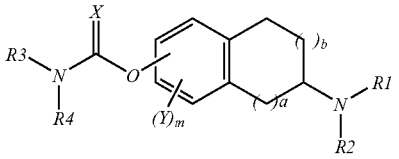

*wherein when a is 0, b is 1 or 2, and when a is 1, b is 1; m is 0–3; X is O or S; Y is halogeno; $R_1$ is hydrogen or $C_{1-4}$ alkyl; $R_2$ is hydrogen, $C_{1-4}$ alkyl, propargyl or substituted propargyl; and $R_3$ and $R_4$ are each independently $C_{1-8}$ alkyl, $C_{6-12}$ aryl, $C_{6-12}$ aralkyl or $C_{6-12}$ cycloalkyl, each of which may be optionally substituted, or hydrogen,*

*such compound being a racemic mixture, an enantiomer, or a salt thereof.*

*30. The compound of claim 29, having the structure:*

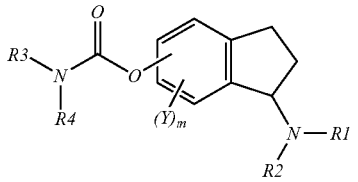

*wherein the group $OC(O)NR_3R_4$ is on the 6 position of the indan ring counting from the amino substituted carbon atom; m is 0; $R_1$ is H; $R_2$ is H; $R_3$ is methyl; and $R_4$ is ethyl.*

*31. The compound of claim 30, wherein the compound is the R enantiomer.*

*32. The compound of claim 29, having the structure:*

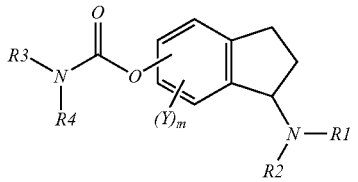

*wherein the group $OC(O)NR_3R_4$ is on the 6 position of the indan ring counting from the amino substituted carbon atom; m is 0; $R_1$ is H; $R_2$ is H; $R_3$ is H; and $R_4$ is ethyl.*

*33. The compound of claim 29, having the structure:*

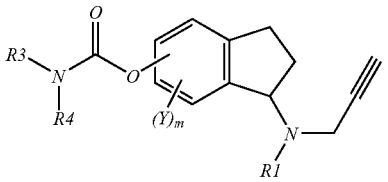

*wherein the group $OC(O)NR_3R_4$ is on the 6 position of the indan ring counting from the amino substituted carbon atom; m is 0; $R_1$ is H; $R_3$ is H; and $R_4$ is ethyl.*

*34. The compound of claim 29, wherein the compound is R-6-(N-methyl, N-ethyl-carbamyloxy)-N'-propargyl-1-aminoindan hemi-(L)-tartrate.*

*35. A pharmaceutical composition comprising the compound of claim 29 and a pharmaceutically acceptable carrier.*

*36. A pharmaceutical composition comprising the compound of claim 30 and a pharmaceutically acceptable carrier.*

*37. A pharmaceutical composition comprising the compound of claim 31 and a pharmaceutically acceptable carrier.*

*38. A pharmaceutical composition comprising the compound of claim 32 and a pharmaceutically acceptable carrier.*

*39. A pharmaceutical composition comprising the compound of claim 33 and a pharmaceutically acceptable carrier.*

*40. A pharmaceutical composition comprising the compound of claim 34 and a pharmaceutically acceptable carrier.*

*41. A method of treating a subject suffering from Alzheimer's disease comprising administering to the subject a therapeutically effective amount of the pharmaceutical composition of claim 35 so as to treat the subject.*

*42. A method of treating a subject suffering from Alzheimer's disease comprising administering to the subject a therapeutically effective amount of the pharmaceutical composition of claim 36 so as to treat the subject.*

*43. A method of treating a subject suffering from Alzheimer's disease comprising administering to the subject a therapeutically effective amount of the pharmaceutical composition of claim 37 so as to treat the subject.*

*44. A method of treating a subject suffering from Alzheimer's disease comprising administering to the subject a therapeutically effective amount of the pharmaceutical composition of claim 38 so as to treat the subject.*

*45. A method of treating a subject suffering from Alzheimer's disease comprising administering to the subject a*

*therapeutically effective amount of the pharmaceutical composition of claim 39 so as to treat the subject.*

*46. A method of treating a subject suffering from Alzheimer's disease comprising administering to the subject a therapeutically effective amount of the pharmaceutical composition of claim 40 so as to treat the subject.*

*47. A method of treating a subject suffering from depression comprising administering to the subject a therapeutically effective amount of the pharmaceutical composition of claim 35 so as to treat the subject.*

*48. A method of treating a subject suffering from depression comprising administering to the subject a therapeutically effective amount of the pharmaceutical composition of claim 36 so as to treat the subject.*

*49. A method of treating a subject suffering from depression comprising administering to the subject a therapeutically effective amount of the pharmaceutical composition of claim 37 so as to treat the subject.*

*50. A method of treating a subject suffering from depression comprising administering to the subject a therapeutically effective amount of the pharmaceutical composition of claim 38 so as to treat the subject.*

*51. A method of treating a subject suffering from depression comprising administering to the subject a therapeutically effective amount of the pharmaceutical composition of claim 39 so as to treat the subject.*

*52. A method of treating a subject suffering from depression comprising administering to the subject a therapeutically effective amount of the pharmaceutical composition of claim 40 so as to treat the subject.*

*53. A method of treating a subject suffering from Attention Deficit Disorder, Attention Deficit and Hyperactivity Disorder, Tourette's syndrome, dementia, neurotraumatic disorder or memory disorder which comprises administering to the subject a therapeutically effective amount of the pharmaceutical composition of claim 35 so as to treat the subject.*

*54. A method of treating a subject suffering from Attention Deficit Disorder, Attention Deficit and Hyperactivity Disorder, Tourette's syndrome, dementia, neurotraumatic disorder or memory disorder which comprises administering to the subject a therapeutically effective amount of the pharmaceutical composition of claim 36 so as to treat the subject.*

*55. A method of treating a subject suffering from Attention Deficit Disorder, Attention Deficit and Hyperactivity Disorder, Tourette's syndrome, dementia, neurotraumatic disorder or memory disorder which comprises administering to the subject a therapeutically effective amount of the pharmaceutical composition of claim 37 so as to treat the subject.*

*56. A method of treating a subject suffering from Attention Deficit Disorder, Attention Deficit and Hyperactivity Disorder, Tourette's syndrome, dementia, neurotraumatic disorder or memory disorder which comprises administering to the subject a therapeutically effective amount of the pharmaceutical composition of claim 38 so as to treat the subject.*

*57. A method of treating a subject suffering from Attention Deficit Disorder, Attention Deficit and Hyperactivity Disorder, Tourette's syndrome, dementia, neurotraumatic disorder or memory disorder which comprises administering to the subject a therapeutically effective amount of the pharmaceutical composition of claim 39 so as to treat the subject.*

*58. A method of treating a subject suffering from Attention Deficit Disorder, Attention Deficit and Hyperactivity Disorder, Tourette's syndrome, dementia, neurotraumatic disorder or memory disorder which comprises administering to the subject a therapeutically effective amount of the pharmaceutical composition of claim 40 so as to treat the subject.*

* * * * *